US007052915B2

(12) United States Patent
Aebersold et al.

(10) Patent No.: US 7,052,915 B2
(45) Date of Patent: May 30, 2006

(54) SELECTIVE LABELING AND ISOLATION OF PHOSPHOPEPTIDES AND APPLICATIONS TO PROTEOME ANALYSIS

(75) Inventors: Ruedi Aebersold, Mercer Island, WA (US); Huilin Zhou, Seattle, WA (US)

(73) Assignee: University of Washington, Seattle, WA (US)

( * ) Notice: Subject to any disclaimer, the term of this patent is extended or adjusted under 35 U.S.C. 154(b) by 35 days.

(21) Appl. No.: 09/880,713

(22) Filed: Jun. 12, 2001

(65) Prior Publication Data

US 2002/0049307 A1 Apr. 25, 2002

Related U.S. Application Data

(60) Provisional application No. 60/210,972, filed on Jun. 12, 2000.

(51) Int. Cl.
G01N 33/50 (2006.01)
G01N 33/533 (2006.01)
G01N 33/534 (2006.01)
G01N 24/00 (2006.01)
C07K 17/02 (2006.01)
C07K 17/14 (2006.01)

(52) U.S. Cl. .......................... 436/86; 435/7.5; 436/173; 436/527; 436/530; 436/544; 436/545; 436/546; 530/408; 530/409; 530/410; 530/811; 530/814

(58) Field of Classification Search .................. 436/86, 436/173, 527, 544, 545, 546, 530, 475, 54; 435/7.5, 188; 530/408, 409, 410, 811, 814
See application file for complete search history.

(56) References Cited

U.S. PATENT DOCUMENTS

| | | | |
|---|---|---|---|
| 4,798,795 A | 1/1989 | Sigler | 435/177 |
| 5,240,859 A | 8/1993 | Aebersold | 436/89 |
| 5,438,017 A | 8/1995 | Allen et al. | 436/89 |
| 5,512,486 A | 4/1996 | Giese et al. | |
| 5,514,559 A | 5/1996 | Marker-Hahn et al. | 435/7.92 |
| 5,527,711 A | 6/1996 | Tom-Moy et al. | 436/518 |
| 5,534,132 A | 7/1996 | Vreeke et al. | 205/777.5 |
| 5,534,440 A | 7/1996 | Aebersold et al. | 436/89 |
| 5,538,897 A | 7/1996 | Yates, III et al. | 436/89 |
| 5,614,368 A | 3/1997 | Ghazarossian et al. | 435/7.5 |
| 5,650,270 A | 7/1997 | Giese et al. | 435/6 |
| 5,658,725 A | 8/1997 | Schlieper et al. | 435/5 |
| 5,686,310 A | 11/1997 | Haystead et al. | 436/86 |
| 5,738,984 A | 4/1998 | Shoseyov | 435/4 |
| 5,851,781 A | 12/1998 | Adamczyk et al. | 435/7.9 |
| 5,856,082 A | 1/1999 | Aebersold et al. | |
| 5,863,740 A | 1/1999 | Kientsch-Engel et al. | 435/7.5 |
| 5,880,270 A | 3/1999 | Berninger et al. | 530/391.1 |
| 5,952,653 A | 9/1999 | Covey et al. | 250/288 |
| 5,958,703 A | 9/1999 | Dower et al. | 435/7.1 |
| 5,965,131 A | 10/1999 | Griffiths et al. | 424/133.1 |
| 5,965,457 A | 10/1999 | Magnani | 436/518 |
| 6,017,693 A | 1/2000 | Yates, III et al. | 435/5 |
| 6,057,096 A | 5/2000 | Rothschild et al. | 435/6 |

FOREIGN PATENT DOCUMENTS

| | | |
|---|---|---|
| WO | WO 90/04786 | 5/1990 |
| WO | WO98/26095 | 6/1998 |
| WO | WO 98/32876 | 7/1998 |
| WO | WO99/02728 | 1/1999 |
| WO | WO00/11208 | 3/2000 |
| WO | WO 00/20870 | 4/2000 |

OTHER PUBLICATIONS

Schurch, S. et al. "Alternative labeling method for peptide ladder sequencing using matrix–assisted laser desorption-ionization Fourier transform mass spectrometry"; *International Journal of Mass Spectrometry and Ion Processes*, Elsevier Scientific Publishing Co., Amsterdam, NL (1997) 169–170:141–152.

Julka, S. et al. "Quantification in Proteomics through Stable Isotope Coding: A Review"; *Journal of Proteome Research* (2003) ppg.A–N.

Wang, P. et al. "Phosphate–specific fluorescence labeling of pepsin by BO–IMI"; *Analytical Biochemistry* (1995) 230:329–332.

Aebersold, R. et al. "Determination of the site of tyrosine phosphorylation at the low picomole level by automated solid–phase sequence analysis" (1991) Anal. Biochem. 199:51–60.

(Continued)

*Primary Examiner*—Mary E. Ceperley
*Assistant Examiner*—Shafiqul Haq
(74) *Attorney, Agent, or Firm*—Greenlee, Winner and Sullivan, P.C.

(57) ABSTRACT

A method for selective labeling of phosphate groups in natural and synthetic oligomers and polymers in the presence of chemically related groups such as carboxylic acid groups. The method is specifically applicable to biological oligomers and polymers, including phosphopeptides, phosphoproteins and phospholipids. In a specific embodiment, selective labeling of phosphate groups in proteins and peptides, for example, facilitates separation, isolation and detection of phosphoproteins and phosphopeptides in complex mixtures of proteins. Selective labeling can be employed to selectively introduce phosphate labels at phosphate groups in an oligomer or polymer, e.g., in a peptide or protein. Detection of the presence of the label, is used to detect the presence of the phosphate group in the oligomer or polymer. The method is useful for the detection of phosphoproteins or phosphopeptides. The phosphate label can be a colorimetric label, a radiolabel, a fluorescent or phosphorescent label, an affinity label or a linker group carrying a reactive group (or latent reactive group) that allows selective attachment of the oligomer or polymer (protein or peptide) to a phosphate label, to an affinity label or to a solid support. The method can be combined with well-known methods of mass spectrometry to detect and identify phosphopeptides and phosphoproteins.

61 Claims, 11 Drawing Sheets

OTHER PUBLICATIONS

Ashikaga, K. et al., "Intramolecular End–to–End Reactions of Photoactive Terminal Groups Linked by Poly(oxyethylene) Chains," (1988) Bull. Chem. Soc. Jpn. 61:2443–2450.

Bayer, E. and Wilchek, M., "Biotin–Binding Proteins: Overview and Prospects," (1990) Methods Enzymol. 184:49–51.

Bennetzen, J.L. and Hall, B.D., "Codon Selection in Yeast," (Mar. 1982) J. Biol. Chem. 257(6):3026–3031.

Boucherie, H. et al., "Two–dimensional gel protein database of *Saccharomyces cerevisiae*" (1996) Electrophoresis 17:1683–1699.

Brockhausen, I. et al., "Control of glycoprotein synthesis," (1989) J. Biol. Chem. 264(19):11211–11221.

Bruce, J.E. et al., "Obtaining More Accurate FTICR Mass Measurements Without Internal Standards using Multiply Charged Ions," (Jan. 2000) J. Am. Soc. Mass Spec. 11(5):416–421.

Bruce, J.E. et al., "High–Mass–Measurement Accuracy and 100% Sequence Coverage of Enzymatically Digested Bovine Serum Albumin from an ESI–FTICR Mass Spectrum," (Jul. 1999) Anal. Chem. 71(14):2595–2599.

Chapman, A. et al., "The primary glycosylation defect in class E Thy–1–negative mutant mouse lymphoma cells is an inability to synthesize dolichol–P–mannose," (1980) J. Biol. Chem. 255(10):4441–4446.

Clauser, K.R. et al., "Rapid mass spectrometric peptide sequencing and mass matching for characterization of human melanoma proteins isolated by two–dimensional PAGE," (1995) Proc. Natl. Acad. Sci. USA 92:5072–5076.

Davis, T. et al., "Rapid Protein Identification Using a Microscale Electrospray LC/MS System on a Ion Trap Mass Spectrometer," (Mar. 1998) J. Am. Soc. Mass. Spec. 9:194–201.

De Leenheer, A.P. and Thienpont, L.M., "Applications of isotope dilution–mass spectrometry in clinical chemistry, pharmacokinetics, and toxicology," (1992) Mass Spectrom. Rev. 11:249–307.

DeRisi, J.L. et al., "Exploring the metabolic and genetic control of gene expression on a genomic scale," (Oct. 1997) Science 278:680–686.

Dongré, A. R. et al., "Emerging tandem–mass–spectrometry techniques for the rapid identification of proteins," (Oct. 1997) Trends Biotechnol. 15:418–425.

Ducret, A. et al., "High throughput protein characterization by automated reverse–phase chromatography/electrospray tandem mass spectrometry," (Mar. 1998) Prot. Sci. 7:706–719.

Duncan, M.W., and Poljak, A., "Amino Acid Analysis of Peptides and Proteins on the Femtomole Scale by Gas Chromatography/Mass Spectrometry" (Mar. 1998) Anal. Chem. 70(5):890–896.

Eng, J. et al. , "An approach to correlate tandem mass spectral data of peptides with amino acid sequences in a protein database," (1994) J. Am. Soc. Mass Spectrum. 5:976–989.

Fenyo, D. et al., "Protein indentification using mass spectrometric information," (May 1998) Electrophoresis 19:998–1005.

Figeys, D. et al., "Electrophoresis combined with novel mass spectrometry techniques: Powerful tools for the analysis of proteins and proteomes," (Jul. 1998) Electrophoresis 19:1811–1818.

Figeys, D. and Aebersold, R., "High sensitivity analysis of proteins and peptides by capillary electrophoresis tandem mass spectrometry: Recent developments in technology and applications," (May 1998) Electrophoresis 19:885–892.

Figeys, D. et al., "Protein identification by solid phase microextraction–capillary zone electrophoresis–microelectrospray–tandem mass spectrometry," (Nov. 1996) Nature Biotech. 14:1579–1583.

Figeys, D. et al., "A microfabricated device for rapid protein identification by microelectrospray ion trap mass spectrometry," (Aug. 1997) Anal. Chem. 69:3153–3160.

Fraser, C.M. et al., "Genomic sequence of a Lyme disease spirochaete, *Borrelia burgdorferi*," (Dec. 1997) Nature 390:580–586.

Freeze, H. H., "Disorders in protein glycosylation and potential therapy: Tip of an iceberg?" (Nov. 1998) J. Pediatrics 133:593–600.

Freeze, H. H., "Human glycosylation disorders and sugar supplement therapy," (Feb. 1999) Biochem. Biophys. Res. Commun. 255:189–193.

Futcher, B. et al., "A Sampling of the Yeast Proteome" (Nov. 1999) Mol. Cell. Bio. 19(11):7357–7368.

Gamper, H.B., "Facile Preparation of Nuclease Resistant 3' Modified Oligodeoxynucleotides," (1993)Nucl. Acids Res. 21(1):145–150.

Garrels, J. I. et al., "Proteome studies of *Saccharomyces cerevisiae*: identification and characterization of abundant proteins." (Aug. 1997) Electrophoresis 18:1347–1360.

Gerber, S.A. et al., "Analysis of rates of multiple enzymes in cell lysates by electrospray ionization mass spectrometry," (Feb. 1999) J. Am. Chem. Soc. 121:1102–1103.

Glaser, L. Phosphomannomutase from yeast. (1966) In Meth. Enzymol. vol. VIII, Neufeld, E. F.; Ginsburg, V. Eds; Academic Press: New York 1966, pp. 183–185.

Gingras, A.C. et al., " Regulation of 4E–BP1phophorylation: a novel two–step mechanism" (Jun. 1999) Genes Dev. 13 (11):1422–1437.

Goffeau et al. , "Life with 6000 Genes," (Oct. 1996) Science 274:546–549.

Goodlett, D.R. et al., "Protein identification with a single accurate mass of a cysteine–containing peptide and constrained database searching" (Mar. 2000) Anal. Chem. 72(6):1112–1118.

Goodlett, D.R. et al., "Quantitative in Vitro kinase reaction as a guide for phosphoprotein analysis by mass spectrometry" (Mar. 2000) Rapid Commun Mass Spectrom. 14(5):344–348.

Goodlett, D.R. et al., "Reduced Elution Speed Detection for Capillary Electrophoresis/Mass Spectrometry," (1993) J. Microcolumn Separations 5:57–62.

Graves, J.D. & Krebs, ED. "Protein phosphorylation and signal transduction" (May 1999) Pharmacol. Ther. 82(2–3):111–121.

Gygi, S.P. et al., "Correlation between protein and mRNA abundance in yeast," (Mar. 1999) Mol. Cell. Biol. 19:1720–1730.

Gygi, S.P. et al., "Protein analysis by mass–spectrometry and sequence database searching: tools for cancer research in the post–genomic era," (Feb. 1999) Electrophoresis 20:310–319.

Gygi, S. P. et al., "Quantitative analysis of complex protein mixtures using isotope–coded affinity tags" (Oct. 1999) Nature Biotechnology 17:994–999.

Gygi, S.P. and Aebersold, R., "Mass spectrometry and proteomics" (Oct. 2000) Curr. Opin. Chem. Biol. 4(5):489–94.

Gygi, S.P. et al., "Measuring gene expression by quantitative proteome analysis" (Aug. 2000) Curr. Opin. Biotechnol. 11(4):396–401.

Haynes, P. A. et al., "Identification of gel–separated proteins by liquid chromatography electrospray tandem mass spectrometry: Comparison of methods and their limitations," (May 1998) Electrophoresis 19:939–945.

Haynes, P.A. et al., "Proteome Analysis: Biological Assay or Data Archive?" (1998) Electrophoresis vol. 19:1862–1871.

Henzel, W.J. et al., , "Identifying proteins from two–dimensional gels by molecular mass searching of peptide fragments in protein sequence databases," (Jun. 1993) Proc. Natl. Acad. Sci. *USA* 90:5011–5015.

Hodges, P.E. et al., "The Yeast Proteome Database (YPD): a model for the organization and presentation of genome–wide functional data," (Jan. 1999) Nucl. Acids. Res. 2(1):69–73.

Horn, D.M.et al., , "A Computer Program for Automated Analysis of High Resolution Mass Spectra," (1998) Proceedings of the 46$^{th}$ ASMS Conf. on Mass Spectrometry and Allied Topics, Orlando, FL May 31–Jun. 4, 1998, p. 118.

Hunter, T. "1001 protein kinases redux—towards 2000" (1994) Semin. Cell Biol. 5:367–376.

Ideker, T. et al., "Integrated genomic and proteomic analyses of a systematically perturbed metabolic network" (May 2001) Science 292(5518):929–34.

Jonscher, K.R. and Yates, J.R. III, "Matrix–assisted laser desorption ionization/quadrupole ion trap mass spectrometry of peptides. Application to the localization of phosphorylation sites on the P protein from Sendai virus" (Jan. 1997) J,. Biol. Chem. 272(3):1735–1741.

Kataky, R. et al., "Comparative Study of Mono– and Di–s-ubstituted 14–Crown–4 Derivatives as Lithium Ionophores," (1990) J. Chem. Soc. Perkin Trans. 2(2):321–327.

Kaur, K. J. and Alton, G.; Hindsgaul, O., "Use of N–acetylglucosaminyl–transerases I and II in the preparative synthesis of oligosaccharides," (1991) Carbohydr. Res. 210:145–153.

Kaur, K. J. and Hingsgaul, O. "A simple synthesis of octyl 3,6–di–O–( –D–mannopyranosyl)– –D–manopyranoside and its use as an acceptor for the assay of N–acetylglucosaminetransferase I activity," (1991) Glycoconjugate J. 8:90–94.

Koch, C.A. et al., "SH2 and SH3 domains: elements that control interactions of cytoplasmic signaling proteins" (1991) Science 252:668–674.

Körner, C. et al., "Carbohydrate–deficient glycoprotein syndrome type V: deficiency of dolichyl–P–Glc:Man$_9$GlcNAc$_2$–PP–dolichyl glucosyltransferase," (Oct. 1998) Proc. Natl. Acad. Sci. U.S.A. 95:13200–13205.

Laemmli, U.K., "Cleavage of Structural Proteins during the Assembly of the Head of Bacteriophage T4," (Aug. 1970) Nature 227:680–695.

Lee et al., "HLA–E Surface Expression Depends on Binding of TAP–Dependent Peptides Derived from Certain HLA Class I Signal Sequences," (Jan. 1998) J. Immunol. 160:4951–4960.

Link, A. J. et al., "Identifying the major proteome components of Haemophilus influenzae type–strain NCTC 8143," (Aug. 1997) Electrophoresis 18:1314–1334.

Link, J. et al., "Direct analysis of protein complexes using mass spectrometry," (Jul. 1999) Nat. Biotech. 17:676–682.

Lundell, N. and Schreitmuller, T., "Sample Preparation for Peptide Mapping—A Pharmaceutical Quality–Control Perspective," (Jan. 1999) Anal. Biochem.266:31–47.

Mann, M. and Wilm, M., "Error–tolerant identification of peptides in sequence databases by peptide sequence tags," (1994) Anal. Chem. 66:4390–4399.

Marshall, A.G. et al., "Fourier Transform Ion Cyclotron Resonance Mass Spectrometry: A Primer," (May 1998) Mass. Spectrom. Rev. 17:1–35.

McMurry, J. E. and Kocovsky, P., "A method for the palladium–catalyzed allylic oxidation of olefins," (1984) Tetrahedron Lett. 25 (38):4187–4190.

McCormack, A.L. et al. "Direct Analysis and Identification of Proteins in Mixtures by LC/MS/MS and Database Searching at the Low–Femtomole Level" (1997) Anal. Chem. 69:767–776.

Morris, A.A.M. and Turnbull, D.M., "Metabolic disorders in children," (1994) Curr. Opin. Neurol. 7:535–541.

Mosely, M.A. et al., "Nanoscale Packed–Capillary Liquid Chromatography Coupled with Mass Spectrometry Using a Coaxial Continuous–Flow Fast Atom Bombardment Interface," (1991) Anal. Chem. 63:1467–1473.

Neubauer, G. et al., "Mass spectrometry and EST–database searching allows characterization of the multi–protein spliceosome complex," (Sep. 1998) Nature Genetics 20:46–50.

Oda, Y. et al., "Accurate quantitation of protein expression and site–specific phosphorylation," (Jun. 1999) Proc. Natl. Acad. Sci. USA 96:6591–6596.

Ogryzko, V.V. et al., "Histone–like TAFs within the PCAF Histone Acetylase Complex" (Jul. 1998) Cell 94:35–44.

Okada, S. and O'Brien, J.S., "Generalized Gangliosidosis: Beta–Galactosidase Deficiency," (1968) Science 160:1002–1004.

Opiteck, G.J. et al., "Comprehensive on–line LC/LC/MS of proteins," (Apr. 1997) Anal. Chem. 69:1518–1524.

Papayannopoulos, I.A., "The interpretation of collision–induced dissociation tandem mass spectra of peptides" (1995) Mass Spectrometry Rev. 14:49–73.

Patterson, S.D. and Aebersold, R., "Mass spectrometric approaches for the identification of gel–separated proteins," (1995) Electro. 16:1791–1814.

Paulsen, H. and Meinjohanns, E., "Synthesis of modified oligosaccharides of N–glycoproteins intended for substrate specificity studies of N–acetylglucos–aminyltransferases II–V," (1992) Tetrahedron Lett. 33(48):7327–7330.

Paulsen, H. et al. "Building units of oligosaccharides: CVII. Synthesis of modified oligosaccarides of N=glycoproteins for substrate specificity studies of N–acetylglucosaminyl-transferase II." (1993) Liebigs Annalen der Chemie 7:721–735.

Pennington, S. R. et al., "Proteome analysis: from protein characterization to biological function," (Apr. 1997) Trends Cell Bio. 7:168–173.

Qin, J. et al., "A strategy for rapid, high–confidence protein identification," (Oct. 1997) Anal. Chem. 69(19):3995–4001.

Qin, J. et al., "De Novo Peptide Sequencing in an Ion Trap Mass Spectrometer with $^{18}$O Labeling" (Jan. 1998) Rapid Communications in Mass Spectrometry 12:209–216.

Qin, J. and Chait, B.T., "Identification and characterization of posttranslational modifications of proteins by MALDI ion trap mass spectrometry" (1997) Anal. Chem. 69(19):4002–4009.

Romanowska, A. et al., "Serological and Structural Features of *Hafnia alvei* Lipopolysaccharides containing D–3–hydroxybutyric Acid," (1994) FEMS Immunol. Med. Microbiol. 8(1):83–88.

Romanowska, A., "Michael Additions for Syntheses of Neoglycoproteins," (1994) Methods Enzymol. 242:90–101.

Ronin, C. et al., "Transfer of glucose in the biosynthesis of thyroid glycoproteins. I. Inhibition of glucose transfer to oligosaccharide lipids by GDP–mannose," (1981) Biochim. Biophys. Acta 674, 48–57.

Ronin, C. et al., "Synthetic substrates for thyroid oligosaccharide transferase. Effects of peptide chain length and modifications in the –Asn–Xaa–Thr– region," (1981) Eur. J. Biochem. 118, 159–164.

Ronne, H., "Glucose repression in fungi," (1995) Trends Genet. 1(1):12–17.

Roth, F.P. et al., "Finding DNA regulatory motifs within unaligned noncoding sequences clustered by whole–genome mRNA quantitation," (Oct. 1998) Nat. Biotechnol. 16:939–945.

Rush, J. S. and Wachter, C. J., "Transmembrane movement of a water–soluble analogue of mannosylphosphoryldolichol is mediated by an endoplasmic reticulum protein," (1995) *J. Cell. Biol.* 130:529–536.

Rush and Wachter, "Method for determination of cellular levels of guanosine–5'–diphosphate–mannose based on a weak interaction with concanavalin A at low pH," (1995) Anal. Biochem. 224(2):494–501.

Schachter, H., "Biosynthetic controls that determine the branching and microheterogeneity of protein–bound oligosaccharides," (1986) Biochem. Cell Biol. 64, 163–181.

Sechi, S. and Chait, B.T., "Modification of cysteine residues by alkylation. A tool in peptide mapping and protein identification," (Dec. 1998) Anal. Chem. 70:5150–5158.

Shalon, D. et al., "A DNA microarray system for analyzing complex DNA samples using two–color fluorescent probe hybridization," (Jul. 1996) Genome Res. 6:639–645.

Shevchenko, A. et al., "Linking genome and proteome by mass spectrometry: large–scale identification of yeast proteins from two dimensional gels," (Dec. 1996) Proc. Natl. Acad. Sci. U.S.A. 93:14440–14445.

Shevchenko, A. et al., "Mass spectrometric sequencing of proteins silver–stained polyacrylamide gels," (Mar. 1996) Anal. Chem. 68:850–858.

Susin et al., "Molecular Characterization of Mitochondrial apoptosis–inducing factor," (Feb. 1999) Nature 397:441–446.

Tan, J. et al., "Mutations in the MGAT2 gene controlling complex glycan synthesis cause carbohydrate deficient glycoprotein syndrome type II, an autosomal recessive disease with defective brain development," (Oct. 1996) Am. J. Hum. Genet. 59:810–817.

Velculescu, V. E. et al., "Characterization of the yeast transcriptome," (Jan. 1997) Cell 88:243–251.

Verma, R. et al. "Phosphorylation of Sic1p by $G_1$ Cdk required for its degradation and entry into S Phase" (1997) Science 278(5337):455–60.

Watts, J.D. et al., "Identification by electrospray ionization mass spectrometry of the sites of tyrosine phosphorylation induced in activated Jurkat T cells on the protein tyrosine kinase ZAP–70" (1994) J. Biol. Chem. 269(47):29520–29529.

Wilbur et al., "Biotin Reagents for Antibody Pretargeting. 2. Synthesis and in Vitro Evaluation of Biotin Dimers and Trimers for Cross–Linking of Streptavidin," (Nov. 1997) Bioconjugate Chem. 8(6):819–832.

Wilbur, D.S. et al., "Biotin Reagents for Antibody Pretargeting. Synthesis, Radioiodination, and in Vitro Evaluation for Water Soluble, Biotinidase Resistant Biotin Derivatives," (1997) Bioconjugate Chem. 8:572–584.

Winger et al., "High–Resolution Accurate Mass Measurements of Biomolecules Using a New Electrospray Ionization Ion Cyclotron Resonance Mass Spectrometer," (1993) J. Am. Soc. Mass Spec. 4:566–577.

Yates, J. R. et al., "Method to correlate tandem mass spectra of modified peptides to amino acid sequences in the protein database," (1995) Anal. Chem. 67:1426–1436.

Zhou, H. et al., "A Systematic approach to the analysis of protein phosporylation" (Apr. 2001) Nature Biotechnol. 19:375–378.

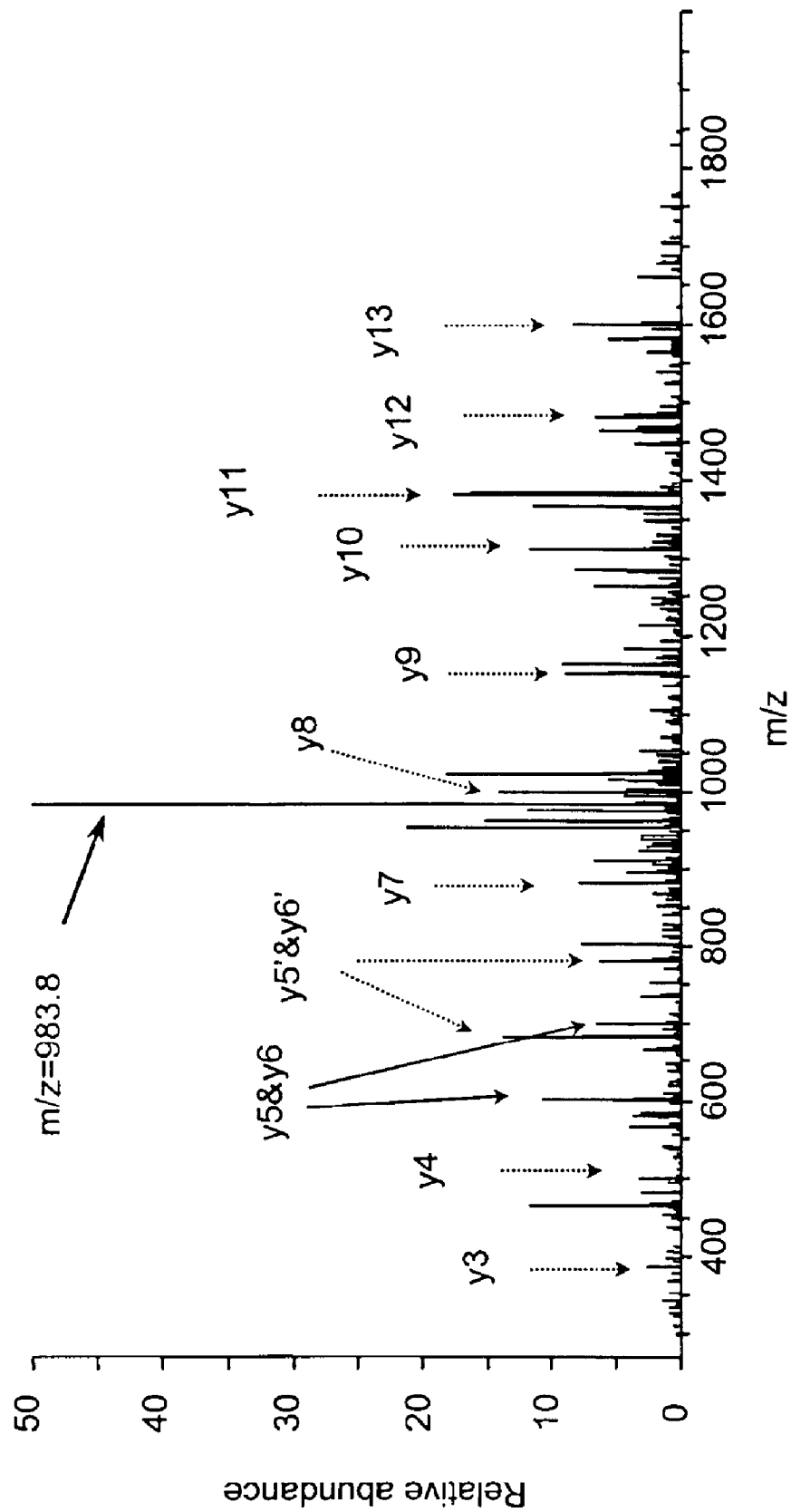

SELECTIVE LABELING AND ISOLATION OF PHOSPHOPEPTIDES AND APPLICATIONS TO PROTEOME ANALYSIS

CROSS-REFERENCE TO RELATED APPLICATIONS

This application takes priority from U.S. provisional application Ser. No. 60/210,972, filed Jun. 12, 2000, which is incorporated by reference herein in its entirety.

STATEMENT REGARDING U.S. GOVERNMENT RIGHTS

This invention was made with U.S. Government support under National Science Foundation grant No. BIR9214821 AM04 and under National Institutes of Health grant no. IR33CA84698. The United States government has certain rights in this invention.

FIELD OF THE INVENTION

A general method for selective chemical labeling of phosphate groups is provided which facilitates highly specific purification of molecules containing one or several phosphate group(s). The method is applicable to the selective labeling of phosphates in phosphoproteins and phosphopeptides. When combined with mass spectrometric techniques, the method can be employed to detect and identify phosphorylated proteins in complex mixtures and to precisely identify the phosphorylated amino acid. The invention has application in the field of proteomics where it facilitates the quantitative, global analysis of protein phosphorylation in a cell or tissue.

BACKGROUND OF THE INVENTION

Proteins are essential for the control and execution of virtually every biological process. The rate of synthesis and the half-life of proteins and thus their expression level are also controlled post-transcriptionally. Furthermore, the activity of proteins is frequently modulated by post-translational modifications, in particular protein phosphorylation, and dependent on the association of the protein with other molecules including DNA and proteins. Neither the level of expression nor the state of activity of proteins is directly apparent from the gene sequence or even from the expression level of the corresponding mRNA transcript. A complete description of a biological system must therefor include measurements that indicate the identity, quantity and the state of activity of the proteins which constitute the system. The large-scale (ultimately global) analysis of proteins expressed in a cell or tissue has been termed proteome analysis (Pennington, S. R., Wilkins, M. R., Hochstrasser, D. F., and Dunn, M. J. (1997), "Proteome analysis: From protein characterization to biological function," Trends Cell Bio. 7:168–173).

At present no protein analytical technology approaches the throughput and level of automation of genomic technology. The most common implementation of proteome analysis is based on the separation of complex protein samples, most commonly by two-dimensional gel electrophoresis (2DE), and the subsequent sequential identification of the separated protein species (Ducret, A. et al. (1998), "High throughput protein characterization by automated reverse-phase chromatography/electrospray tandem mass spectrometry," Prot. Sci. 7:706–719; Garrels, J. I. et al. (1997), "Proteome studies of Saccharomyces cerevisiae: identification and characterization of abundant proteins. Electrophoresis," 18:1347–1360; Link, A. J. et al. (1997), "Identifying the major proteome components of Haemophilus influenzae type-strain NCTC 8143," Electrophoresis 18:1314–1334; Shevchenko, A. et al. (1996), "Linking genome and proteome by mass spectrometry: large-scale identification of yeast proteins from two dimensional gels," Proc. Natl. Acad. Sci. U.S.A. 93:14440–14445; Gygi, S. P. et al. (1999), "Correlation between protein and mRNA abundance in yeast," Mol. Cell. Biol. 19:1720–1730; Boucherie, H. et al. (1996), "Two-dimensional gel protein database of Saccharomyces cerevisiae," Electrophoresis 17:1683–1699).

The 2DE approach has been revolutionized by the development of powerful mass spectrometric techniques and computer algorithms which correlate protein and peptide mass spectral data with sequence databases and, thus, rapidly and conclusively identify proteins (Eng, J., McCormack, A., and Yates, J. I. (1994), "An approach to correlate tandem mass spectral data of peptides with amino acid sequences in a protein database," J. Am. Soc. Mass Spectrom. 5:976–989; Mann, M., and Wilm, M. (1994), "Error-tolerant identification of peptides in sequence databases by peptide sequence tags," Anal. Chem. 66:4390–4399; Yates, J. R. et al. (1995), "Method to correlate tandem mass spectra of modified peptides to amino acid sequences in the protein database," Anal. Chem. 67:1426–1436).

This technology has reached a level of sensitivity which now permits the identification of essentially any protein which is detectable by conventional protein staining methods including silver staining (Figeys, D., and Aebersold, R. (1998), "High sensitivity analysis of proteins and peptides by capillary electrophoresis tandem mass spectrometry: Recent developments in technology and applications," Electrophoresis 19:885–892.; Figeys, D. et al. (1998), "Electrophoresis combined with mass spectrometry techniques: Powerful tools for the analysis of proteins and proteomes," Electrophoresis 19:1811–1818; Figeys, D. et al. (1997), "A microfabricated device for rapid protein identification by microelectrospray ion trap mass spectrometry," Anal. Chem. 69:3153–3160; Figeys, D. et al. (1996), "Protein identification by solid phase microextraction-capillary zone electrophoresis-microelectrospray-tandem mass spectrometry," Nature Biotech. 14:1579–1583; Shevchenko, A. et al. (1996), "Mass spectrometric sequencing of proteins silver-stained polyacrylamide gels," Anal. Chem. 68:850–858). However, the sequential manner in which samples are processed limits the sample throughput. The most sensitive methods have been difficult to automate and low abundance proteins, such as regulatory proteins, escape detection without prior enrichment, thus effectively limiting the dynamic range of the technique. In the 2DE-based approach proteins are quantified by densitometry of stained spots in the 2DE gels.

The development of methods and instrumentation for automated, data-dependent electrospray ionization (ESI) tandem mass spectrometry ($MS^n$) in conjunction with microcapillary liquid chromatography (μLC) and database searching has significantly increased the sensitivity and speed of the identification of gel-separated proteins. As an alternative to the $2DE/MS^n$ approach to proteome analysis, the direct analysis by tandem mass spectrometry of peptide mixtures generated by the digestion of complex protein mixtures has been proposed (Dongr'e, A. R. et al. (1997), "Emerging tandem-mass-spectrometry techniques for the rapid identification of proteins," Trends Biotechnol. 15:418–425). μLC-Ms/MS has also been used successfully for the large-scale identification of individual proteins directly from mixtures without gel electrophoretic separation (Link, J. et al. (1999), "Direct analysis of large protein complexes using mass spectrometry," Nat. Biotech.17:676–682; Opiteck, G. J. et al. (1997), "Comprehensive on-line LC/LC/MS of proteins," Anal. Chem. 69:1518–1524.)

While these approaches dramatically accelerate protein identification, the quantities of the analyzed proteins cannot be easily determined due to the observation that mass spectrometers are inherently not quantitative devices. Direct mass spectrometric analysis of protein mixtures by mass spectrometry can be made quantitative by the application of stable isotope dilution theory, whereby two chemically identical analytes (one representing an internal standard and the sample to be measured) are labeled with stable isotope tags of identical chemical composition but different mass. This principle has been implemented in quantitative proteome analysis by the development of a class of chemical reagents termed isotope coded affinity tags (ICAT). (Gygi, S. P. et al. (1999), "Quantitative analysis of complex protein mixtures using isotope-coded affinity tags," *Nat. Biotechnol.* 17, 994–999.) ICAT reagents and their application to the analysis of complex protein mixtures have been shown to substantially alleviate the dynamic range problem encountered by the 2DE/Ms" approach.

Protein phosphorylation is one of the most important regulatory events in cells. The state of activity of numerous enzymes and processes and the association of specific proteins into functional complexes are frequently controlled by reversible protein phosphorylation (Graves, J. D. & Krebs, E. D. (1999), "Protein phosphorylation and signal transduction," *Pharmacol. Ther.* 82, 111–121; Koch, C. A. et al. (1991)," SH2 and SH3 domains: elements that control interactions of cytoplasmic signaling proteins," *Science* 252, 668–674; Hunter, T. (1994), "1001 protein kinases redux-towards 2000," *Semin. Cell Biol.* 5, 367–376). The principle goals of studying protein phosphorylation are the identification, quantitation and determination of the biological function of phosphorylation site(s) in phosphoproteins. Much of the difficulty in such studies lies in the fact that many phosphoproteins exist only at very low abundance. Further, proteins are often phosphorylated at a low stoichiometry and at multiple sites. Therefore, it is usually difficult to obtain sufficient amounts of pure phosphoprotein for such analyses. All current methods for the analysis of the phosphorylation state of proteins focus on one purified phosphoprotein at a time (Verma, R. et al. (1997), "Phosphorylation of Siclp by Gl Cdk required for its degradation and entry into S phase," *Science* 278, 455–60; Watts, J. D. et al. (1994), "Identification by electrospray ionization mass spectrometry of the sites of tyrosine phosphorylation induced in activated Jurkat T cells on the protein tyrosine kinase ZAP-70," *J. Biol. Chem.* 269, 29520–29529; Gingras, A. C. et al. (1999), "Regulation of 4E-BP1 phosphorylation: a novel two-step mechanism," *Genes Dev.* 13, 1422–1437). Because cellular proteins are coordinately phosphorylated to control specific biological processes, the complex mechanisms that control biological systems by protein phosphorylation are difficult to investigate using current technology.

Because phosphopeptide(s) typically are infrequent and of low abundance in protein digests, highly purified or enriched phosphopeptide samples are needed for mass spectrometric analysis. The need to selectively enrich for phosphopeptides prior to MS analysis is particularly urgent if a protein mixture rather than a single purified phosphoprotein is being analyzed. In addition, no MS-based method to quantify protein phosphorylation directly is currently available. Quantitative study of protein phosphorylation often involves methods such as $^{32}P$ radiolabeling (Oda, Y. et al. (1999), "Accurate quantitation of protein expression and site-specific phosphorylation," Proc. Natl. Acad. Sci. USA 96:6591–6596). Therefore, an MS-based method that allows both the identification of the sites of phosphorylation from complex mixtures of proteins and their quantitation will be an essential part of proteome analysis.

Thus, there is a substantial need in the art for a more rapid and general method for the analysis of protein phosphorylation, particularly in complex protein mixtures, that does not require purification to homogeneity of individual phosphoproteins. The present invention provides such a method.

SUMMARY OF THE INVENTION

This invention provides a method for selective labeling of phosphate groups in natural and synthetic oligomers and polymers in the presence of chemically related groups such as carboxylic acid groups. The method is specifically applicable to biological oligomers and polymers, including phosphopeptides, phosphoproteins and phospholipids. Selective labeling of phosphate groups in proteins and peptides, for example, facilitates separation, isolation and detection of phosphoproteins and phosphopeptides in complex mixtures of proteins. Selective labeling can be employed to selectively introduce phosphate labels at phosphate groups in an oligomer or polymer, e.g., in a peptide or protein. Detection of the presence of the label is used to detect the presence of the phosphate group in the oligomer or polymer. The method is of particular use for the detection of phosphoproteins or phosphopeptides. The phosphate label can be a colorimetric label, a radiolabel, an isotope label, a fluorescent or phosphorescent label, an affinity label or a linker group carrying a reactive group (or latent reactive group) that allows selective attachment of the oligomer or polymer (protein or peptide) to a phosphate label, to an affinity label or to a solid phase material.

Selective attachment of a phosphate group to its affinity label or selective attachment to a solid support allows selective isolation of an oligomer or polymer (e.g., protein or peptide) that carries at least one phosphate group. The presence of an affinity label allows capture of the selectively labeled oligomer or polymer using a capture reagent that specifically bonds to the affinity label. The presence of a linker that allows selective covalent attachment of the oligomer or polymer to a solid surface allows physical separation of the selectively labeled oligomer or polymer from non-selectively labeled (non-phosphorylated) species in a sample. The method is particularly useful for the selectively labeling of proteins and peptides having a phosphate group (phosphoproteins and phosphoptides) in the presence of carboxylic acid groups. The method of this invention can be used specifically to separate phosphoproteins and phosphopeptides from mixtures of non-phosphorylated proteins mixtures of non-phosphorylated proteins and/or nonphosphorylated peptides and thus to overcome detection problems due to low levels of these species in samples.

In specific embodiments the method is applied to the separation, detection and identification of phosphopeptides and phosphoproteins in one or more samples. The method can simply be used to selectively introduce a phosphate label that allows detection of the presence of one or more phosphate groups in a peptide or protein. The method can also be used to selectively introduce an affinity label at a phosphorylation site in a peptide or a protein or selectively bond a phosphoprotein or phosphopeptide to a solid surface.

When combined with well-known methods of mass spectrometry, the selective labeling method of this invention facilitates separation of phosphopeptides from mixtures and facilitates their detection by mass spectrometry and facilitating sequencing of the peptides by tandem mass spectrometry. Art-known methods can be applied to identify phosphoproteins in a sample from the sequences of phosphopeptides detected in a sample. When combined with methods for differential isotopic labeling, the method of this invention can be employed to quantify relative amounts of phosphopeptides and phosphoproteins in different samples. These quantitative methods allow a comparison of phosphorylation state in samples derived from different sources (e.g., from different cell-types or different organisms), samples that are differentially affected by a stimulus (e.g., administration of a drug or contact with a potentially toxic material), by a change in environment (e.g., nutrient level, temperature, passage of time) or by a change in condition or cell state (e.g., disease state, malignancy, site-directed mutation, gene knockouts) of a cell, tissue or organism from which the sample originated. The phosphoproteins identified in such a screen can function as markers for the changed state. Phosphopeptides and phosphoproteins from any naturally-occurring environment or artificially-controlled environment can be assessed by the methods herein. The method can be applied to mixtures of naturally-occurring proteins or peptides, as well as to mixtures of proteins or peptides derived from recombinant or synthetic methods.

The selective labeling method of this invention comprises the following steps as applied to phosphopeptides and phosphoprotein:

(1) the carboxylic acid groups in proteins or peptides in one or more samples containing proteins are permanently selectively protected so that any phosphate groups in the proteins or peptides in the sample (s) are unprotected (remain as free phosphate groups);

(2) the free phosphate groups in the proteins or peptides of the sample(s) are then selectively reacted with a label (e.g., a phosphate label, a radio label, isotope label, or an affinity label) or with a linker carrying a reactive group or a latent reactive group that will facilitate selective attachment of phosphoproteins or phosphopeptides to a label or to a solid surface; and (3a) selectively labeled proteins or peptides are detected using the presence of the label as a measure of the presence of at least one phosphate group; or (3b) selective attachment of peptides or proteins to an affinity label or to a solid surface to facilitate selective isolation of phosphopeptide and/or phosphoproteins separated from proteins and peptides that do not have a phosphate group.

In a preferred embodiment, selective labeling of phosphate groups is accomplished by initial reaction of the proteins and peptides in one or more samples with a protective group, such as an amine, that reacts in the presence of a condensation catalyst with and protects both carboxylic acid groups and phosphate groups. Amines react with carboxylic acid (or the corresponding esters) to form amide bonds. Amines react with phosphates or phosphate ester groups to form phosphoramide bonds. The labeled phosphoramide bonds in the protected proteins and peptides are then selectively cleaved with a reagent that does not cleave amide bonds. This results in the regeneration of free phosphate groups which can be selectively labeled or linked to a solid surface. In a specific embodiment, an amine, such as ethanolamine, can be used for initial protection of all carboxylic acid and all phosphate groups. For example, a carbodiimide catalyzed condensation of an amine with the peptide or protein forms amide and phosphoramide bonds. Ethanolamine can be selectively cleaved from the phosphate groups of the protein or peptide by treatment with mild acid conditions (e.g., trifluoroacetic acid (tfa), 10–30% by volume in water, exemplifying mild acid conditions). Excess protecting agent (e.g., excess amine) can removed by extensive washing of the peptides on a reverse phase column. In specific embodiments, the free phosphate is reacted with a linker group that carries a reactive functional group including a latent reactive group (such as a sulfhydryl group) that can be used to attach the phosphoprotein or phosphopeptide to a solid support or used for selective labeling of phosphopeptides and phosphoproteins with a phosphate label. For example, carbodiimide-catalyzed condensation reactions can be used to attach cystamine to free phosphate groups. The disulfide bond in the cystamine can be cleaved to generate a reactive sulfhydryl group. (Cystamine is an example of a group that carries a latent reactive group).

Phosphopeptides or phosphoproteins that have been selectively separated and isolated from other proteins or peptides in a sample are cleaved from the affinity label or solid support and analyzed by conventional mass spectrometric techniques including tandem mass spectrometry to detect, identify by sequencing or quantitate the phosphopeptides or phosphoproteins in one or more samples.

Proteins and/or peptides in different samples can be differentially isotopically labeled to facilitate comparison of amounts of the same peptide or protein in different samples. Isotopic labeling is typically introduced at the carboxylic acid protective groups (e.g., at amine groups such as ethanolamine).

In this method, amine groups in the proteins or peptides are preferably also treated with a protective group selective for reaction with the amine side groups of amino acids (e.g., the $\epsilon$-amino group of lysine side chains, and/or peptide $\alpha$-amino groups). This treatment controls crosslinking of amine side chains during sample preparation. If sulfhydryl linker groups are employed, it is preferred that the samples be treated with a reagent that reduces disulfide bonds. Selectively labeled samples are also optionally treated with hydroxyamine to remove tyrosine adducts that may have formed during sample preparation.

This invention also provides kits for selective labeling of phosphate groups which contain reagents needed to carry out selective labeling and optionally contain positive and negative controls for use with the kit reagents. A reagent kit comprises a carboxylic acid/phosphate reactive protective group and a label or linker group that is to be selectively bonded to the phosphate groups in the phosphoproteins or phosphopeptide. The kit also contains any catalysts or condensation agents needed to facilitate the reaction (e.g., carbodiimide). In addition, the kit optionally includes a reagent for selective cleavage of phosphoramide bonds in the presence of amide bonds (e.g., a dilute acid that can be used to generate the mild acidic conditions for selective cleavage). Kits can include reagents in premeasured aliquots for assay of a selected number of samples.

The label may be an affinity label and, if so, the kit preferably contains a capture reagent appropriate for use with the affinity label. A kit optionally contains protective groups for amines (e.g., t-boc or f-moc), and solid phase materials. The kit may further contain a set of differentially isotopically labeled protective groups, linkers affinity labels, or other labels (fluorescent, chromophoric or phosphorescent) to allow quantitative determination of the amounts (or relative amounts ) of phosphoproteins and phosphopeptides in different samples. With respect to fluorescent, chromophoric, radiolabels or other labels, different types of labels can be used to label the phosphates in different samples. For example, different fluorescent labels that are separately detectable and can be individually quantitated (e.g., fluorescein amine, rhodamine amine) can be used to label different samples and to detect relative amounts of labeleled peptides in difference samples. Kits further optionally contain instructions for carrying out selective labeling, as well as directions for conducting various types of analysis that can be used in combination with the kit to detect, identify, or quantitate phosphopeptides and phosphoproteins.

In specific embodiments this invention provides:

A method for selectively labeling or tagging phosphate groups in one or more natural or synthetic peptides or proteins in the presence of one or more carboxylic acid groups by reacting the natural or synthetic peptides or proteins with a protective group that reacts to protect the phosphate groups therein by forming phosphoramide bonds and to protect the carboxylic acid groups therein by forming amide bonds; thereafter treating the protected peptide or protein under conditions which selectively substantially cleave the phosphoramide bond, without substantially cleaving the amide bond to regenerate free phosphate groups in the peptide or protein; and reacting the free phosphate groups in the peptide or protein, in which the carboxylic acids groups remain protected, with a label or tag comprising a functional group that reacts with a phosphate or with a linker that comprises two or more functional groups that function to bond a phosphopeptide or phosphopeptide to a solid support.

Reagents which substantially cleave one bond in the substantial absence of cleavage of the other exhibit at least about a 10:1 ratio of cleavage of one bond to another (measured in terms of the rate of reaction or the amount of cleavage product detected) and preferably exhibit at least about a 20:1 ratio, and more preferably, at least about a 100:1 ratio of cleavage of one bond to the other. Of course applications to the methods herein, the reagents for selective cleavage of bonds are preferably chosen to cleave one bond without any measurable cleavage of the other bond.

In this method the phosphopeptide or phosphoproteins can be covalently attached to a solid support material through reaction with a sulfhydryl group of the linker and the solid support can comprise immobilized iodoacetyl groups for reaction with sulfhydryl groups. In this method phosphopeptides or phosphoproteins can be separated from a mixture by attachment to a solid support or by binding of the phosphopeptides to a capture reagent via an affinity label.

A method for detecting one or more phosphopeptides in one or more samples containing a mixture of peptides by selectively protecting the carboxylic acid groups of the peptides in the one or more samples such that any phosphate groups in the peptides remain unprotected; selectively labeling the unprotected phosphate groups in the peptides in the sample with a label having a functional group that reacts directly or indirectly with a phosphate; detecting the peptides carrying the label to detect the phosphopeptides in the sample. The label can be a radiolabel, an isotope label, a fluorescent label, a calorimetric label or an affinity label. the label can also be a reactive label which carries at least one reactive group or at least one latent reactive group. A latent reactive group is a group that must be activated for reaction, e.g., it can be a group that carries a protective group and which becomes reactive on removal of the protective group.

In this method tandem mass spectrometry can be used to determine the amino acid sequence of peptides and the precise position of the phosphorylated amino acid within the peptide sequence. Quantitation of the relative amounts of phosphopeptide can be accomplished by use of differentially isotopically labeled labels or tags. Tandem mass spectrometry can also be used to detect one or more phosphopeptides in a sample and determine the relative amounts of one or more phosphopeptides in the two or more samples by measuring the relative amounts of differentially isotopically labeled labels or tags present in the one or more samples.

The method also provides kits for selectively labeling phosphopeptides in a mixture of peptides by reacting the peptides in one or more samples with a protective group which reacts with a carboxylic acid or ester thereof and which also reacts with a phosphate group; and employing an acid reagent for selectively regenerating free phosphate groups in the peptide by reacting the protected peptides under sufficiently mild acid conditions such that the phosphoramide bond is substantially cleaved and the amide bond is substantially not cleaved. The kit can further comprise any one or more of the following: a radiolabel, a stable isotope label, a fluorescent label, a colorimetric label, an affinity label, a capture reagent with a corresponding affinity label, a reactive label, protective groups for amine groups, one or more solid supports, an iodoacetylated solid support, one or more enzymes for carrying out a protein digest; and reagents for carrying out the various enzymatic or chemical reactions of the detection or separation methods herein.

BRIEF DESCRIPTION OF THE DRAWINGS

FIG. 4A is an ion chromatogram of 1 pmol of β-casein digest before phosphopeptide isolation. The peak at m/z=1031.6 represents the doubly charged form of the expected phosphopeptide of the β-casein tryptic digest. FIG. 4B is an ion chromatogram of the isolated phosphopeptides of the β-casein tryptic digest. The peak at m/z=1182.5 represents the doubly charged form of the same tryptic phosphopeptide from β-casein, indicated in FIG. 4A, but additionally modified on its seven carboxylate groups with ethanolamine. FIG. 4C is the CID spectrum of β-casein digest in FIG. 4B. The peak at m/z=938.0 represents the doubly charged form of the selected parent ion (m/z=1031.6) minus the $H_3PO_4$ group. FIG. 4D is the CID spectrum of isolated phosphopeptides of the β-casein digest in FIG. 4C. Again, the peak at m/z=1133.6 represents the double charged form of the selected parent ion (m/z=1182.5) minus $H_3PO_4$, and the y-ion series used for peptide identification is indicated. The b-ion series are much less intense and are omitted for clarity.

FIG. 5A is an LC-MS ion chromatogram of the phosphopeptides isolated from a tryptic digest of protein mixture generated from in vitro kinase reaction between Lck and MBP. FIG. 5B is a CID mass spectrum of the most intense ion (m/z=630.1, 2+ion). This peak was subjected to CID analysis and database searching, which identified the peptide as THY*GSLPQK from MBP, with the tyrosine residue being phosphorylated.

FIGS. 6A–C illustrate the results of phosphopeptide isolation from a yeast cell lysate. FIG. 6A is an LC-MS chromatogram of the phosphopeptides isolated from a tryptic digest of whole yeast cell lysate. FIG. 6B is an integrated mass spectrum of ions eluting from the LC column with retention times between 24.7 and 26.5 min, as indicated in FIG. 6A Major ion peaks that additionally exhibited a loss of 98 Da on CID, indicating that they are phosphopeptides, are annotated with an asterisk (*). FIG. 6C is the CID spectrum recorded for the peptide peak indicated in FIG. 6B at m/z±1032.7. This spectrum was sufficient to identify the phosphopeptide as TAGIQIVADDLT*VT*NPAR from enolase. However, the exact site of threonine phosphorylation was not unambiguously defined because of the difficulty in assigning y5 and y6 ions. Both potential locations for the phosphate have thus been indicated (*), although the parent ion mass confirms the peptide as a singly phosphorylated species.

DETAILED DESCRIPTION OF THE INVENTION

Figure 1:
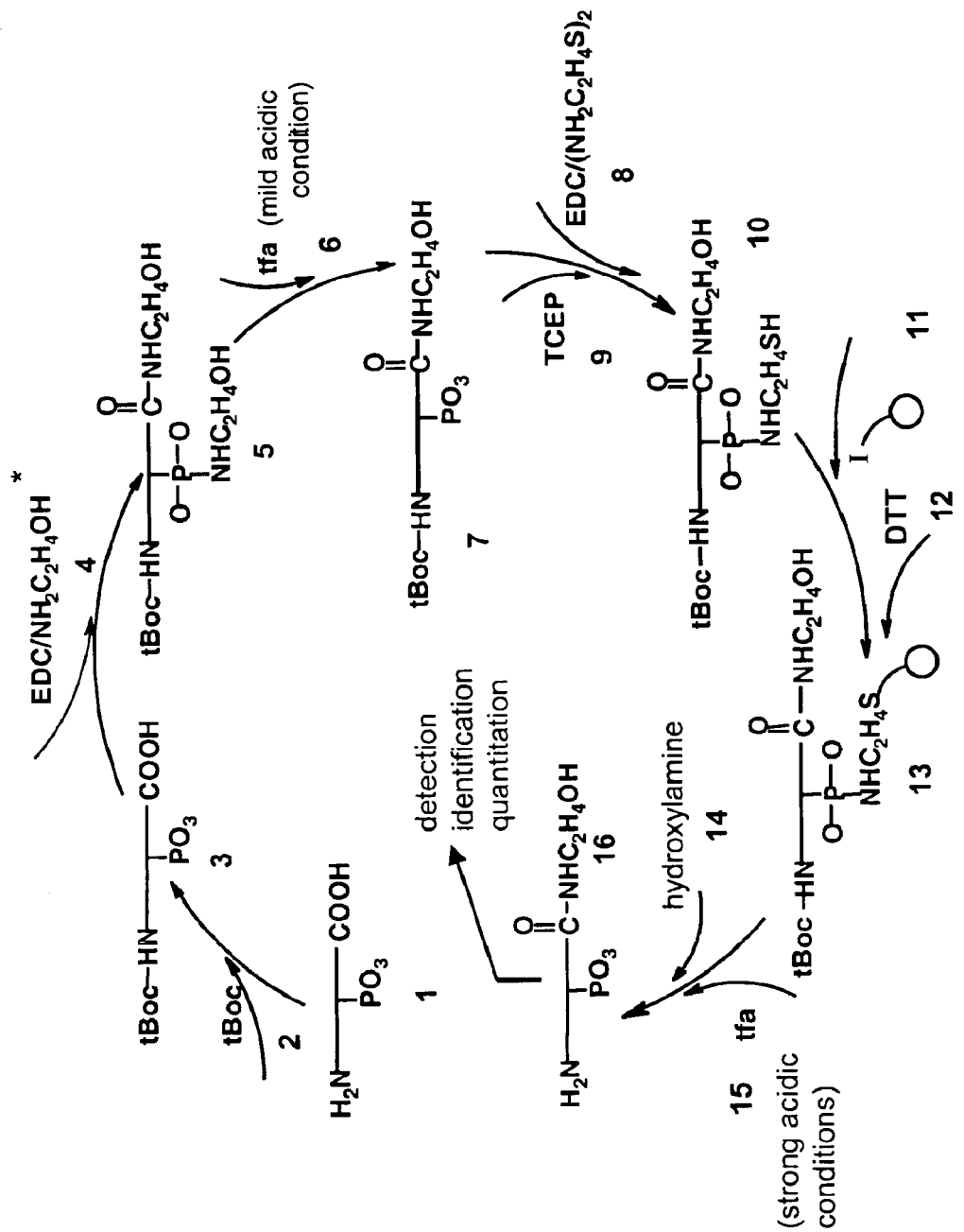
FIG. 1 is a scheme illustrating the chemistry of phosphopeptide/phosphoprotein labeling and purification of this invention.

This invention provides methods for detecting the presence of phosphopeptides and phosphoproteins in a mixture, identifying phosphopeptides and phosphoproteins that are present in a mixture and determining the relative amounts of phosphopeptides and phosphoproteins in one or more mixtures. The methods are based on the ability to selectively form covalent bonds to phosphate groups of peptides in the presence of carboxylic acid (or ester) groups and amine groups of peptides. The methods are more specifically based on the ability to selectively bond a label or linker to a phosphate group in the presence of carboxylic acids. In particular, the method relies on the ability to cleave phosphoramide bonds under mild acid conditions which do not cleave amide bonds. Thus, selective labeling or linking to a phosphate group in the method proceeds by initial conversion of peptide and protein carboxylic acid groups (of the C-terminus and amino acid side groups) to amides and the conversion of phosphate groups of peptides and proteins to phosphoramidate. Thereafter, the phosphoramidate are selectively cleaved without cleaving the amides and the free phosphate groups are reacted with selected labels or linkers to facilitate detection, identification and quantitation of phosphopeptides in one or more samples.

A preferred method for forming amide and phosphoramide bonds is by condensation with free amines. Condensation can be accomplished using various condensation catalysts known in the art, but the use of carbodiimide is a preferred method. In general any amine can be employed but alkanol amines, such as ethanolamine are preferred. The amine can function simply as a protecting group to facilitate selective reaction with phosphate groups, it can carry a detectable label, e.g., carry a group or moiety that can be detected, such as a radiolabel, a fluorescent label or the like, or it can carry a group or moiety that can react (a reactive functionality), a group that can be made to react (a latent reactive group) or that can form a bond or complex to another species (e.g., an affinity label which will bond or complex to a capture reagent).

Phosphoramide bonds are selectively cleaved in the presence of amide bonds by use of mild acid conditions. Both the strength of the acid and the length of time of expose to acidic conditions can be controlled to obtain selective cleavage of the phosphoramide bonds. A preferred treatment uses dilute trifluoroacetic acid, e.g., 10% or less by volume in water for a selected time up to several hours. Thereafter the free-phosphate group can be reacted with a variety of labels or linkers. For example, the presence of a phosphopeptide in a sample can be detected by the presence of a selected label that has been selectively attached to a phosphate group. Phosphopeptides can be separated from non-phosphorylated peptides by selective attachment to a solid support, for example, via a linker group that is selectively attached to the phosphate group. Selective attachment of phosphopeptides to a solid support can be used to isolate and purify phosphopeptide in one or more samples and facilitate their detection and identification by analytical methods, particularly by mass spectrometry.

In a specific embodiment of the methods herein, a peptide mixture, which may be generated from a variety of natural or synthetic sources, is treated to protect amine groups in the peptides (N-terminal as well as those in amino acid side groups). Amines are preferably protected using t-Boc chemistry as is known in the art. Carboxylic acids and phosphate groups of amine-protected peptides are then condensed with free amine, preferably ethanolamine (which may be isotopically labeled) to form amides and phosphoramidates, respectively. Differential isotopic labeling of different samples of peptides is accomplished by treating different samples with differentially labeled amines, e.g., non-deuterated ethanolamine can be used for one sample and deuterated ethanolamine can be used for a second sample. Other stable isotope encoded amine reagents can be used.

The peptides which are amine-protected and in which the carboxylic acid groups and any phosphate groups have been converted to amides and phosphoramidites, respectively, are then treated under mild acid conditions to selectively cleave the phosphoramide bonds leaving the amide bonds substantially intact. Any phosphopeptides in a sample carry free phosphate groups and the phosphopeptides in different samples are differentially isotopically labeled. The phosphopeptides in each sample can then selected attached to a solid support, via a sulfhydryl linker generated by condensation of the phosphate groups with cystamine. The attached cystamines are then reduced to generate free sulfhydryl groups which can react with iodoacetyl groups on a solid support. The cystamine functions as a latent reactive group which is activated for attachment to the solid support by reduction (e.g., with dithiothreitol, DTT or tris[2-carboxlethylphosphine], TCEP).

Phosphopeptides in samples are attached to the solid support and after extensive washing are cleaved off the support (e.g., using trifluoroacetic acid). Preferably, the amine protective groups are cleaved in this reaction as well. These steps provide purified, isotopically labeled phosphopeptides which can be subjected to tandem mass spectrometric analysis. CID mass spectra provide the sequence of any phosphopeptide present in a sample and indicate the presence and location of phosphorylated amino acid residues. Using the peptide sequence information obtained, database searching can be performed to determine the protein source of the phosphopeptides detected. The relative signal intensities of differentially isotopically labeled phosphopeptides in different samples detected in mass scans in the same mass spectrometer allow measurement of the ratio of abundance of the labeled phosphopeptides in different samples.

The methods of this invention have several advantages. Amine groups of the peptides are protected and do not form amide bonds with the carboxylic acid groups of other peptides minimizing peptide cross-linking and other artifactual reactions. The carboxylic acid groups remain protected and thus can provide for differential isotope labeling.

Covalent linkage of the amine labeling the phosphate group to a solid support is a preferred implementation of the method of this invention because it allows stringent washing of the immobilized phosphopeptides and their specific release by acid treatment. The use of cysteine to label phosphate groups is preferred because any peptide with residual unblocked carboxylic acid groups, whether it contains phosphate or not, will be converted into sulfhydryl groups and remain attached to the solid support irreversibly. The presence of cysteine residues interferes with the above method, however, cysteine groups can be optionally alkylated by iodoacetamide or any other known alkylating reagent. Before any protein sample is subjected to this method of phosphopeptide isolation, it can be reduced by dithiothreitol, and then alkylated by excess of iodoacetamide under denaturing condition. The solid phase-based embodiment of the method of this invention therefore serves as an efficient way for highly specific phosphopeptide purification and the stable isotope tags introduced by carboxyl group derivatization serves as the basis for relative phosphopeptide quantitation. Any solid material that can be derivatized with functional groups that facilitate attachment of the phosphopeptides (e.g., via sulfhydryl groups) and that is otherwise relatively inert with respect to the peptides, reagents and washing conditions of the method can be used. For example, any solid phase material that is useful in solid phase peptide synthesis can be employed. Glass beads are a preferred solid phase material.

With respect to fluorescent, chromophoric, radiolabels or other labels, different types of labels can be used to label the phosphates in difference samples. For example, different fluorescent labels that are separately detectable and can be individually measured (e.g., fluorescein amine, rhodamine amine) can be used to label different samples and to detect relative amounts of labeled peptides in different samples. These labels can also be used to separate the peptides by RP-HPLC or CE (capillary electrophoresis) and to detect the relative amounts of peptides by fluoresence measurement. To implement quantitative measurement of relative amounts of peptides in difference samples, it is preferred to calibrate the system to account for differences in detection of the different labels. For example, is it preferred when using different fluorescent labels to calibrate for differences in quantum yields of different labels.

FIG. 1 illustrates the selective labeling method of this invention. As illustrated, peptides (1) are first reacted with an amine protective group (2), such as tBoc(t-Butoxydicarbonate). A variety of useful amine protective groups are known in the art and readily available for application in this method. The protective group selected must be compatible with other reagents used in the method. Peptides protected amine groups (3) are then treated with a reagent that reacts to protect carboxylic acid and phosphate groups (4), such as an amine. An amine group will react with a carboxylic acid group to form an amide (—CO—NH—) bond or with a phosphate group to form a phosphoramide (—PO$_2$—NH—) bond. The fully protected peptide (5) is treated to selectively cleave the phosphoramide bond to remove protection from the phosphate group. Mild acid conditions (6) are used to selectively regenerate the phosphate group. For example, the protected peptide can be treated with trifluoroacetic acid (tfa) (about 30% or less by volume in water for about 1 hour, preferably about 20% in water for about 1 hour, and more preferably 10% for 30 min. at room temperature). Mild acidic conditions include the use of a strong acid, such as tfa, in diluted form. Other mild acidic conditions that will achieve the desired chemistry can be determined by routine experimentation in which treatment is varied to maximize phosphoramide cleavage and minimize amide cleavage.

Protected peptides in which the phosphate protective groups have been removed (7) are treated to selectively label the free phosphate group. For example, a linker containing a sulfhydryl (8) or other reactive group can be selectively bonded to the phosphate groups. The linker group contains functionality for bonding to the phosphate group (e.g., an amino group) and functionality for linking to a label or to a solid surface. Alternatively, at this point in the method, a label (an affinity label or any phosphate label such as a fluorescent label or radiolabel) carrying functionality for bonding to the phosphate group can be directly attached to the phosphate. As illustrated in FIG. 1, the functionality on the linker group may be a latent functional group which must be activated prior to reaction to add a label or to covalently attach to a solid surface. In the illustrated case, cystamine carries a latent sulfhydryl functional group (a —S—S- bond) which is activated by addition of a reducing agent (9, such as TCEP or DTT) that reduces disulfide bonds.

FIG. 1 illustrates covalent linkage of phosphopeptides via the sulfhydryl functional group on the linker. The peptides carrying the sulfhydryl group linker (10) are reacted with derivatized beads carrying iodoacetyl groups (11). A variety of types of solid materials are available for use in this method. Solid phase materials (in the form of beads, surfaces, layers, etc.) are derivatize to facilitate linkage. After reaction with phosphopeptide (10), remaining reactive groups on the solid can be capped or protected with an appropriate capping reagent (e.g., with DTT (12)). Phosphopeptides covalently linked to the solid support (13) can be physically separated from other peptides in the samples and any non-specifically attached peptide can be removed with washing.

FIG. 1 illustrates a step of treating the bound phosphopeptides with hydroxylamine (14). More specifically, beads carrying bound peptide (13) are washed and incubated in 1 M hydroxylamine (14, pH 10.0) for about 2 hrs. to regenerate tyrosine, since tyrosine residues can form adducts with carbodiimide. This step is optional, but preferred, when carbodiimide reagents are employed in the method, to regenerate tyrosines in the bound peptide which may have formed adducts with the carbodiimide reagent. It has been found that treatment with 5% hydroxylamine for about 30 min. is sufficient to regenerate tyrosine.

Unbound peptides are removed by sequential washing with 5 M sodium chloride, acetonitrile and water. The volume of each washing step will minimally consist of about 10 column bed volumes, but larger volumes can also be employed. The bound phosphopeptides are then treated under strong acid conditions (15) to cleave the linker to the solid surface and to remove the amine protective group (2). The carboxylic acid groups of the free (i.e., released) phosphopeptide (16) are, however, still protected. These protective groups can be employed to carry differential isotopic labels that are useful for quantitative peptide analysis to by mass spectrometry. It may also be desirable to employ conditions that will selectively cleave the phosphopeptide from the solid support without cleavage of the amine reactive protective group (2). A variety of protective groups which are cleaved using a variety of different conditions are available in the art. One of ordinary skill in the art can select a protective group, a linker and cleavage conditions that will allow retention of an amine reactive protective group on cleavage of the linker from the solid support material. If the amine reactive protective group is retained after cleavage of the peptide from the solid surface, it can also be used for differentially isotopic labeling.

Dried separated phosphopeptides are resuspended in water for LC-MS analysis Phosphopeptides selectively labeled and isolated by the method herein are preferably analyzed by mass spectrometric techniques. Protective groups and linkers used in this method are preferably selected so that any modifications to the peptide that are retained on release from the solid phase material do not significantly interfere with mass spectral analysis and sequencing of the peptide by tandem mass spectrometric methods.

U.S. patent application Ser. No. 09/383,062 filed Aug. 25, 1999, and corresponding International Patent Application WO99/19415, filed Aug. 25, 1999, having inventors in common with this application, provide analytical reagents and mass spectrometry-based methods for the rapid, and quantitative analysis of proteins or protein function in mixtures of proteins. The methods employ reagents designated "affinity-labeled protein reactive reagents" that allow for the selective isolation of a peptide from complex mixtures. The reagent contains an affinity label covalently linked through a linker group to a protein reactive group that selectively reacts with certain protein functional groups. The linker may be differentially isotopically labeled. The reagents and methods can be applied to the detection and identification of proteins in complex mixtures of proteins, where the peptides isolated by the method are characteristic of the presence of a protein in the mixture. Isolated peptides are characterized by mass spectrometric (MS) techniques. In particular, the sequence of isolated peptides can be determined using tandem MS (MS$^n$) techniques, and by application of sequence database searching techniques, the protein from which the sequenced peptide originates can be identified. The affinity-labeled protein reactive reagents can also provide for differential isotopic labeling of the isolated peptides to facilitate quantitative determination of the relative amounts of proteins in different samples and provide for internal standards to facilitate quantitative determination of the absolute amounts of one or more proteins present in a sample. The present invention provides a method for selective labeling of phosphopeptides in complex mixtures and their selective isolation that can be employed with the methods and applications described in U.S. patent application Ser. No. 09/383,062 US and International Patent Application WO 99/19415. These patent applications are incorporated by reference herein in their entirety to the extent that they are not inconsistent with the disclosures herein, among other things for descriptions of differential isotopic labeling, mass spectrometric methods and application of the selective labeling methods described.

The following references relate to the application of mass spectrometric techniques to protein identification, particularly with respect to proteome analysis: Ideker T., et al. (May 4, 2001) "Integrated genomic and proteomic analyses of a systematically perturbed metabolic network." Science 292 (5518):929–34; Gygi S. P., Aebersold R. (October 2000) "Mass spectrometry and proteomics." Curr Opin Chem Biol. 4(5):489–94.; Gygi, S. P., et al. (August 2000) "Measuring gene expression by quantitative proteome analysis" Curr Opin Biotechnol." 11(4):396–401; Goodlett, D. R., et al. (May 15, 2000) "Protein identification with a single accurate mass of a cysteine-containing peptide and constrained database searching." Anal Chem. 72(6):1112–8.; and Goodlett, D. R., et al., (2000) "Quantitative in vitro kinase reaction as a guide for phosphoprotein analysis by mass spectrometry," Rapid Commun Mass Spectrom. 14(5):344–8; Zhou, H. et al (April 2001) Nature Biotechnol. 19:375–378. These reference are incorporated by reference herein to the extent that they are not inconsistent with the disclosure of this application.

Peptide mixtures subjected to the method of this invention can be generated from natural or synthetic samples and may be the results of chemical, physical or enzymatic digestion of protein samples. Proteins can be digested using any enzymatic appropriate method, such as trypsin digestion. Peptides in the digest preferably range in size from about 10 to about 50 amino acids in length and are more preferably sized to facilitate peptide sequencing using tandem mass spectrometric methods. Those of ordinary skill in the art can select a protein digestion protocol suitable for use in protein sample(s) of interest.

Amines are preferred reagents for selective labeling of carboxylic acids in the presence of phosphate groups. Any amine reagent will generally provide the function of this protective group. Alkanolamines, such as ethanolamine are preferred amine reagents. One of ordinary skill in the art will appreciate that other reagents can be found which provide a similar selective labeling function. One or ordinary skill in the art can identify and select other reagents for selectively labeling without resort to undue experimentation. The protective group employed must, however, also be suitable for use in the reactions of this invention. Any art-known methods and reagents suitable for selective protection of carboxylic acid groups as described herein are intended to be encompassed by this invention. With respect to amines that are used to selectively protect carboxylic acid groups, the reaction of amines with carboxylic acids and phosphate groups is preferably done in the presence of a coupling agent. Coupling agents that can be used in this reaction include, among others, dicyclohexylcarbodiimide, or 2,3,5, 6-tetrafluorophenyl trifluoroacetate. In addition, a coupling catalyst such as 4-dimethylaminopyridine can be employed.

The selective labeling method of this invention employs a treatment that selectively removes protection from phosphate groups, but not carboxylic acid groups. In particular, the protected peptides are treated with acidic conditions that cleave phosphoamidate bonds, but not amide bonds (herein mild acidic conditions). Treatment under these mild acidic conditions cleaves the phosphoamide bonds between phosphate and ethanolamine without deprotecting the amine and carboxylic acid groups of the peptide. For example, tBoc protection remains mostly intact, unless prolonged acid treatment is involved. Those of ordinary skill in the art will appreciate that other treatment conditions may be found which provide for a similar function. One or ordinary skill in the art can identify and select other reagents for selectively removal of protecting groups on phosphates without resort to undue experimentation. Any such methods and reagents known in the art which achieve the selective removal of phosphate protective groups as described herein are intended to be encompassed by this invention.

If desired, selectively labeled peptides can be attached to a solid support by attaching a linker group carrying an appropriate functional group for bonding to the support. Attachment of phosphopeptides to solid supports is exemplified by attachment via sulfhydryl group reaction with iodine. Those of ordinary skill in the art appreciate that functional groups other than sulfhydryl and iodine can be used to complete a linkage to a solid support material. A variety of methods for making such attachments are known in the art. Any method and reagents that achieve the function of selective attachment of the phosphopeptide to a solid support are intended to be encompassed by this invention.

The method of this invention as specifically exemplified employs steps of washing peptides on reverse phase columns to remove undesired materials from the peptide sample. Those of ordinary skill in the art will appreciate that methods for removing such materials other than those specifically described herein are known in the art and can be readily applied to the method herein to achieve the desired result. All such art-known methods for washing or removal of undesired materials are intended to be encompassed by this invention.

Figure 2:
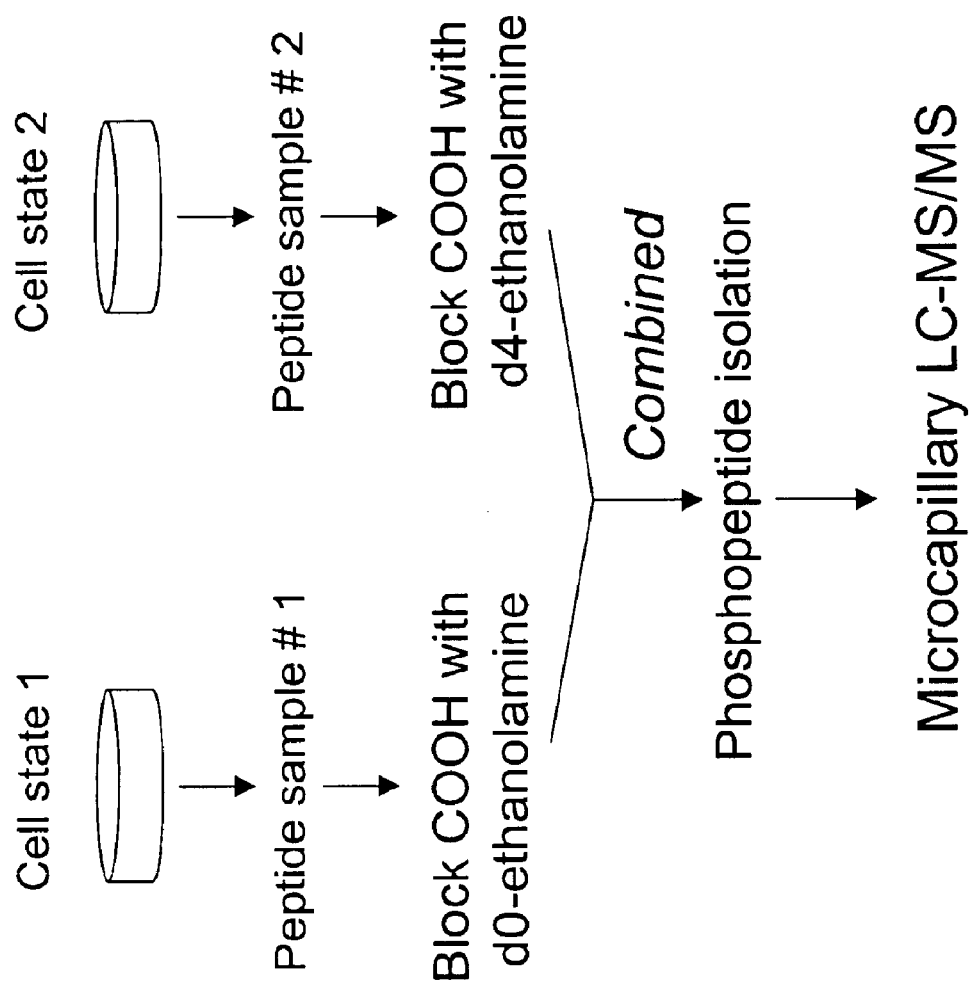
FIG. 2 is a flow chart illustrating quantitative comparison of phosphopeptides and phosphoproteins in two different samples.

A strategy for quantitative, comparative analysis of protein phosphorylation in one or more samples is illustrated in FIG. 2. Peptide samples are prepared from two cell states (1 and 2). As an example, differentially isotopically labeled carboxylic acid/phosphate group amine protective reagents (one for each sample, e.g., d0- or d4-ethanolamine for each of two samples) are used to differentially isotopically label all carboxylic acid groups and initially any phosphates in peptide samples. Carboxyl groups include the C-terminus of a peptide and the side chains of glutamic acid and aspartic acid residues (as well as any carboxylic acid side groups from rare or non-naturally-occurring amino acids). Ethanolamine groups protecting the phosphate groups are selectively removed to generate free phosphate groups. Free phosphate groups are then derivatized with a linker that facilitates separation of phosphopeptides. For every phosphopeptide ultimately purified using this method, there is at least one labeled protective group (e.g., ethanolamine) attached to the C-terminus of the peptide. Dependent upon its structure, a given phosphopeptide may have more than one labeled protective group.

The mass difference between differentially isotopically labeled peaks will depend on the isotopic mass difference among the labels and the charge state of the peptides, which can be determined in the mass spectrometer itself based on the natural isotope distribution. Since isotopic-related peptides essentially co-elute from a microcapillary high performance liquid column chromatography (HPLC) run, as they are analyzed by the mass spectrometer, multiplets of peaks due to a given peptide appear for each differentially labeled peptide (e.g., a doublet for two samples labeled differentially with d0- and d4-ethanolamine). The relative intensity of the peaks in the multiplet (e.g., doublet) of peaks from the same peptide in differentially isotopically labeled samples directly yields the relative concentrations of that peptide in the different samples. The underlying principle of this quantification method is that isotopically related peptides are chemically identical and therefore represent a perfect mutual internal standard. The intensities of the signals generated in the mass spectrometer from the differentially isotopically labeled peptides from different samples precisely reflect relative quantities of the peptide molecules present in those samples, respectively.

The sequence of a phosphopeptide and the identification of the site(s) of phosphorylation can be determined by a combination of tandem mass spectrometry and computer-assisted database search programs, such as SEQUEST (Trademark, University of Washington, Seattle Wash.) (McCormack, A. L. et al. (1996) "Direct Analysis and Identification of Proteins in Mixtures by LC/MS/MS and Database Searching at the Low-Femtomole Level", Anal. Chem. 69, 767–776; Eng, J. K. et al. (1994)" An Approach to Correlate Tandem Mass Spectral Data of Peptides with Amino Acid Sequences in a Protein Database" J. Amer. Soc. Mass. Spectrom., 5, 976–989; U.S. Pat. No. 5,538,897 (Jul. 23, 1996) Yates, III et al.) In the first stage of a tandem mass spectrometer, any given phosphopeptide is selected and subjected to collision induced dissociation (CID). The spectra of a resulting fragment ion is recorded in the second stage of the mass spectrometry, as a so-called CID spectrum. This process is repeated with other (ideally all) peptides present in the sample. Because the CID process usually causes fragmentation at peptide bonds and different amino acids for the most part yield peaks of different masses, a CDI spectrum alone often provides enough information to determine a peptide sequence. Peptide sequencing and protein identification is facilitated by using a sequence searching computer program, such as SEQUEST™, which takes all known genomic sequences, computes all possible theoretical CID spectra and compares them to experimental CID spectra for matches and sequence identification. The mass modification to the C-terminus, glutamic acid, aspartic acids and any other acidic side groups are known and this information can be incorporated into the computer analysis. Also mass changes due to phosphorylation are also known and can be incorporated into the computer analysis. Data can be searched for any possible phosphorylations to serine, tyrosine, and threonine residues, thus allowing the identification of sites of phosphorylation.

The methods of this invention can employ protective groups which are isotopically labeled to generate pairs or sets of reagents that are substantially chemically identical, but which are distinguishable by mass. For example a pair of protective group reagents, one of which is isotopically heavy and the other of which is isotopically light can be employed for the comparison of two samples, one of which may be a reference sample containing one or more known proteins in known amounts. For example, any one or more of the hydrogen, nitrogen, oxygen or sulfur atoms in the protective group may be replaced with their isotopically stable isotopes: $^2$H, $^{13}$C, $^{15}$N, $^{17}$O, $^{18}$O or $^{34}$S. Differential isotopic labeling is preferably introduced into the peptides of this invention in the carboxylic acid protective group.

The methods of this invention can use affinity labels or phosphate labels for the detection or separation of phosphopeptide. The methods of this invention can use any phosphate label, including, but not limited to radiolabels, fluorescent labels, colorimetric labels, etc. The label is selectively attached to a phosphate in a phosphopeptide in the sample and its detection detects the presence of the phosphate.

Suitable affinity labels bind selectively either covalently or non-covalently and with high affinity to a capture reagent (CR). The CR-A interaction or bond should remain intact after extensive and multiple washings with a variety of solutions to remove non-specifically bound components. The affinity label binds minimally or preferably not at all to components in the assay system, except CR, and does not significantly bind to surfaces of reaction vessels. Any non-specific interaction of the affinity label with other components or surfaces should be disrupted by multiple washes that leave CR-A intact. Further, it must also be possible to disrupt the interaction of A and CR to release peptides, substrates or reaction products, for example, by addition of a displacing ligand or by changing the temperature or solvent conditions. Preferably, neither CR or A react chemically with other components in the assay system and both groups should be chemically stable over the time period of an assay or experiment. The affinity label is preferably soluble in the sample liquid to be analyzed and the CR should remain soluble in the sample liquid even though attached to an insoluble resin such as Agarose or controlled pore glass. With respect to CR, the term soluble means that CR is sufficiently hydrated or otherwise solvated such that it functions properly for binding to A. CR or CR-containing conjugates should not be present in the sample to be analyzed, except when added to capture A. Affinity labels useful in this invention contain functionality that allows them to be bonded (preferably via a covalent bond which can be selectively cleaved, if and when desired) to a phosphate group.

Examples of A and CR pairs include:

d-biotin or structurally modified biotin-based reagents, including d-iminobiotin, which bind to proteins of the avidin/streptavidin, which may, for example, be used in the forms of strepavidin-Agarose, oligomeric-avidin-Agarose, or monomeric-avidin-Agarose;

any 1,2-diol, such as 1,2-dihydroxyethane ($HO-CH_2-CH_2-OH$), and other 1,2-dihyroxyalkanes including those of cyclic alkanes, e.g., 1,2-dihydroxycyclohexane which bind to an alkyl or aryl boronic acid or boronic acid esters, such as phenyl-$B(OH)_2$ or hexyl-$B(OEthyl)_2$ which may be attached via the alkyl or aryl group to a solid support material, such as Agarose;

maltose which binds to maltose binding protein (as well as any other sugar/sugar binding protein pair or more generally to any ligand/ligand binding protein pairs that has properties discussed above);

a hapten, such as dinitrophenyl group, for any antibody where the hapten binds to an anti-hapten antibody that recognizes the hapten, for example the dinitrophenyl group will bind to an anti-dinitrophenyl-IgG;

a ligand which binds to a transition metal, for example, an oligomeric histidine will bind to Ni(II), the transition metal CR may be used in the form of a resin bound chelated transition metal, such as nitrilotriacetic acid-chelated Ni(II) or iminodiacetic acid-chelated Ni(II);

glutathione which binds to glutathione-S-transferase.

The covalent attachment of A to CR can be accomplished, for example, by the reaction of iodoacetamide on CR with a sulfhydryl group on A.

In general, any A-CR pair commonly used for affinity enrichment which meets the suitability criteria discussed above can be employed. Biotin and biotin-based affinity tags are preferred. Of particular interest are structurally modified biotins, such as d-iminobiotin, which will elute from avidin or strepavidin columns under solvent conditions compatible with ESI-MS analysis, such as dilute acids containing 10–20% organic solvent. It is expected that d-iminobiotin tagged compounds will elute in solvents below pH 4. d-Iminobiotin tagged protein reactive reagents can be synthesized by methods described herein for the corresponding biotin tagged reagents.

A displacement ligand, DL, is optionally used to displace A from CR. Suitable DLs are not typically present in samples unless added. DL should be chemically and enzymatically stable in the sample to be analyzed and should not react with or bind to components (other than CR) in samples or bind non-specifically to reaction vessel walls. DL preferably does not undergo peptide-like fragmentation during MS analysis, and its presence in sample should not significantly suppress the ionization of tagged peptide, substrate or reaction product conjugates.

DL itself preferably is minimally ionized during mass spectrometric analysis and the formation of ions composed of DL clusters is preferably minimal. The selection of DL depends upon the A and CR groups that are employed. In general, DL is selected to displace A from CR in a reasonable time scale, at most within a week of its addition, but more preferably within a few minutes or up to an hour. The affinity of DL for CR should be comparable or stronger than the affinity of the tagged compounds containing A for CR. Furthermore, DL should be soluble in the solvent used during the elution of tagged compounds containing A from CR. DL preferably is free A or a derivative or structural modification of A. Examples of DL include, d-biotin or d-biotin derivatives, particularly those containing groups that suppress cluster formation or suppress ionization in MS.

The method of this invention can employ linker groups which bond to phosphate groups to attach the phosphopeptide to a solid support. A linker can also be used to attach an affinity label or phosphate label to a phosphopeptide. Any linker used should preferably be soluble in the sample liquid to be analyzed and it should be stable with respect to chemical reaction, e.g., substantially chemically inert, with components of the sample as well as with any other reagents used in the method. The linker when bound to the peptide should not interfere with the specific interaction of an affinity label with a CR and should bind minimally or preferably not at all to other components in the system, to reaction vessel surfaces or CR. Any non-specific interactions of the linker should be broken after multiple washes.

Samples that can be analyzed by methods of this invention include cell homogenates; cell fractions; biological fluids including urine, blood, and cerebrospinal fluid; tissue homogenates; tears; feces; saliva; lavage fluids such as lung or peritoneal lavages; mixtures of biological molecules including proteins, lipids, carbohydrates and nucleic acids generated by partial or complete fractionation of cell or tissue homogenates.

The methods of this invention employ mass spectrometric and tandem mass spectrometric methods. While a variety of MS methods are available and may be used in these methods, Matrix Assisted Laser Desorption Ionization MS (MALDI/MS) and Electrospray Ionization MS (ESI/MS) methods are preferred.

The method of this invention is illustrated and exemplified by application to the detection and identification of phosphopeptides in a phosphopeptide standard sample, (Example 2, FIGS. 3A–C); an enzymatic digest of a single phosphoprotein, β-casein (Example 3, FIGS. 4A–4D); a protein phosphorylated in vitro at a tyrosine residue (Example 4, FIGS. 5A–C), a digest of total lysate of yeast cells (Example 5, FIGS. 6A–C and Table 1); and a digest of total lysate of Jurkat cells (Table 2).

The following examples are intended to further illustrate the invention and are not intended to limit the invention.

EXAMPLES

Example 1: Phosphopeptide Isolation Procedure

Peptide samples were dried, and then subjected to the method shown in FIG. 1A according to the following steps. 1) Peptide mixture was resuspended in 50% (v/v) of 0.1 M phosphate buffer (pH 11)/acetonitrile. 0.1 M of t-Butyl-dicarbonate (tBoc) was added for 4 hours at room temperature. 2) Acetonitrile was removed under reduced pressure. Samples were made to 1 M ethanolamine, 25 mM N-hydroxysuccinimide (NHS) and 0.5 M of N,N'-dimethylaminopropyl ethyl carbodiimide HCl (EDC) and incubated 2 hours at room temperature. 3) 10% trifluoroacetic acid (TFA) was added for 30 minutes at room temperature. Longer treatment under these conditions did not detrimentally affect the results. Samples can be neutralized at this point, but neutralization as found to have no significant effect on results. Samples were then desalted on and recovered from a C18 column (Waters Associates, Milford, Mass. WAT 023590) using elution with 80% acetonitrile, 0.1% TFA. 4) Peptides were dried and redissolved in 1 M imidazole (pH 6.0). Imidazole is optional and was employed to inhibit possible carbodiimide adduct formation with sensitive amino acids such as histidine. 0.5 M EDC was added for 3 hours at room temperature. Samples were loaded on a C18 column, washed with water and treated with 1 M cystamine (pH 8.0) for 2 hours at 50° C. on the column. Peptide were washed with water and reduced with 10 mM DTT to generate free sulfhydryl groups. 5) After washing to remove DTT, peptides were eluted with 80% acetonitrile, 0.1% TFA and incubated with 20 mg beads with immobilized iodoacetyl groups for at least 2 hours at pH 8.0 (titrated with 1 M Tris pH 8.0, 50 mM EDTA). Beads with immobilized iodoacetyl groups were prepared by a 2-hour reaction between 3 equivalents of iodoacetic anhydride and 1 equivalent of amino beads (Sigma, G4643) with 3.3 equivalent of diisopropylethylamine in dimethylformide. The formation of a tyrosine adduct with carbodiimide is a possible side reaction. Such an adduct is unstable against nucleophiles such as hydroxylamine. Therefore, after attachment of phosphopeptide to the beads 1 M hydroxylamine (pH 10) was used to incubate beads for 2 hours at room temperature. This restored tyrosine residues. It has been found that treatment with 5% hydroxylamine solution for 30 min. is typically sufficient to restore tyrosine residues. Beads were then washed sequentially with 2 M NaCl, methanol and water to remove nonspecifically bound molecules. 6) The beads were incubated with 100% TFA for 30 minutes to recover phosphopeptides. Concurrently, tBoc protection was removed. The recovered sample was dried under reduced pressure and resuspended in water for LC-MS/MS analysis.

Example 2

Figure 3C:
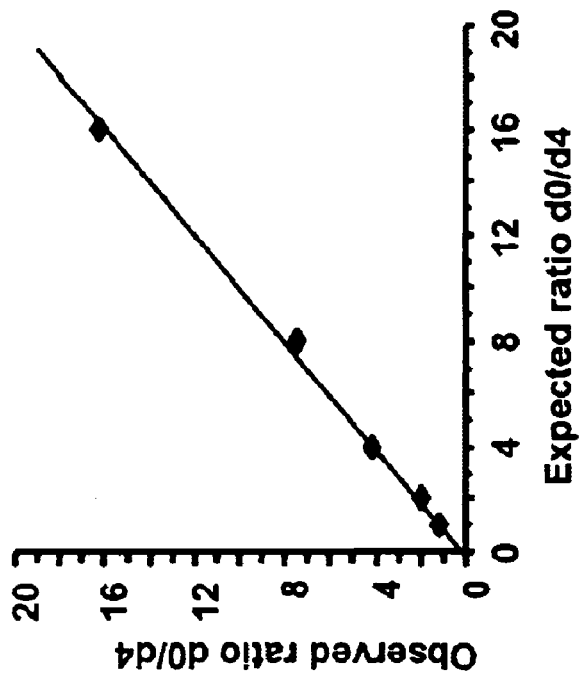
FIGS. 3A–C illustrates the results of mass spectrometric analysis of differentially labeled samples of phosphoangiotensin as described in Example 1 and Example 2.
Figure 3B:
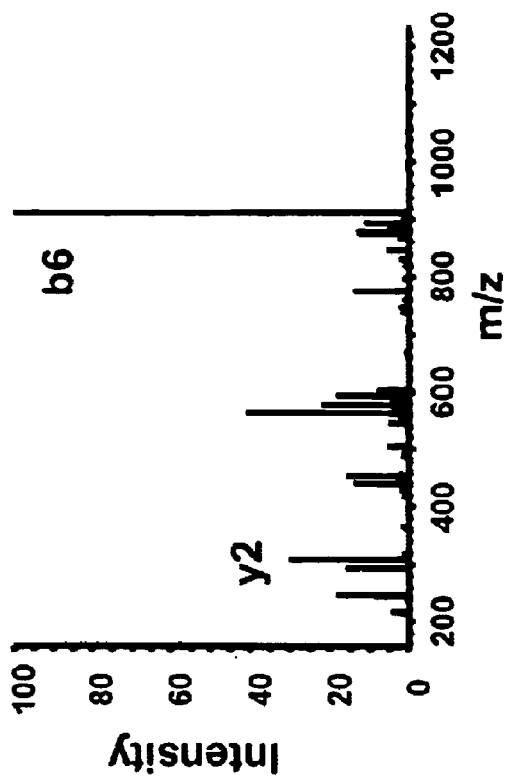
Figure 3A:
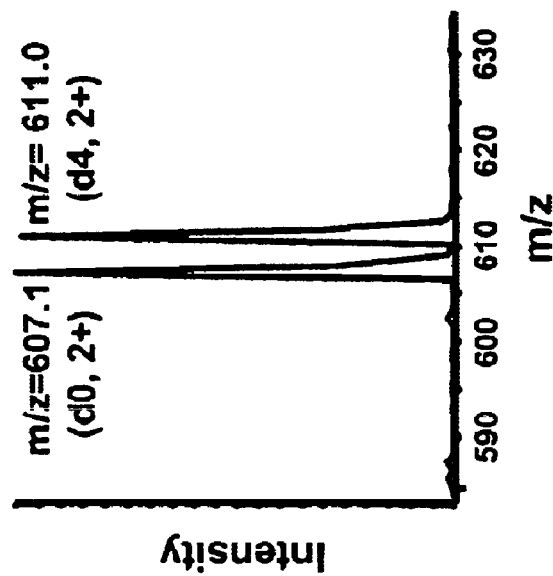

Two separate samples of equal amounts of phosphoangiotensin peptide were analyzed by the method of this invention. The carboxylic acid groups in the two different samples were blocked (leaving phosphate groups free as described above) by either light ethanolamine (d0-ethanolamine) or heavy ethanolamine (d4-ethanolamine, $HOCD_2CD_2NH_2$). Phosphoangiotensin contains two carboxylic acid groups, so that the mass difference for the $[M+2H]^{2+}$ ion is 4 for the differentially labeled peptides. The results of mass spectrometric analysis of the differentially labeled samples that were subjected to selective labeling and separation of phosphopeptides of this invention is illustrated in FIGS. 3A–C. A doublet of peaks $[M+2H]^2+$ at m/z=607 and 611, due to light and heavy labeled samples, respectively, is observed as expected. Further the relative ratios of the two peaks is about 1:1 as expected. The CID spectrum of these peaks is similar to that of the unprotected peptide, except for the fragment ions that are mass shifted by the modification (label attachment). Modifications to the carboxylic acid groups used to achieve differential labeling do not adversely affect the quality of the CID spectrum that would be used to identify the sequence of unknown peptides.

Phosphopeptide isolation was performed essentially as in Example 1 with minor modifications. Peptides were suspended in 50% (v/v) acetonitrile and 0.1 M potassium phosphate buffer (pH 11). t-Butyloxy-carbonyl (t-Boc, 1 M) was added for 4 h at room temperature. Acetonitrile was removed under reduced pressure. The amine-protected peptide was dried under reduced pressure and resuspended in 1 M ethanolamine HCl. The pH of the solution was adjusted to approximately 6 by addition of 50 mM N-hydroxy succinimide (NHS). N,N'-demethylaminopropylethyl carbodiimide-HCl (EDC) was added (5 mg/50 μL) for 4 h at room temperature. Amine-protected peptide was labeled with the heavy ethanolamine (d4-ethanolamine, $HOCO_2CD_2$—$NH_2$) in a similar manner.

Phosphates were selectively deprotected in the differentially isotopically labeled peptides by mixing each solution containing the labeled peptide with an equal volume of 20% (v/v) trifluoroacetic acid for 1 h and thereafter neutralizing the reactions using 2 M sodium phosphate buffer. The neutralized solution was loaded on a reverse phase C18 column and washed extensively with water. The peptide with regenerated phosphate groups was eluted from the C-18 column using 80% (v/v) acetonitrile in water and then dried. Samples of heavy and light isotopically labeled peptide were combined for mass spectrometric analysis.

An LCQ ion trap mass spectrometer (Finnigam MAT, San Jose, Calif.) was used with an HP1100 solvent delivery system (Agilent, Palo Alto, Calif.). Peptides were pressure-loaded onto the column, then eluted and analyzed by microcapillary LS-MS/MS as described in Gygi, S. P. et al. 1999 supra. The collision energy or the LCQ was set at 30%.

Example 3: Isolation of Phosphopeptides from β-casein

Figure 4A:
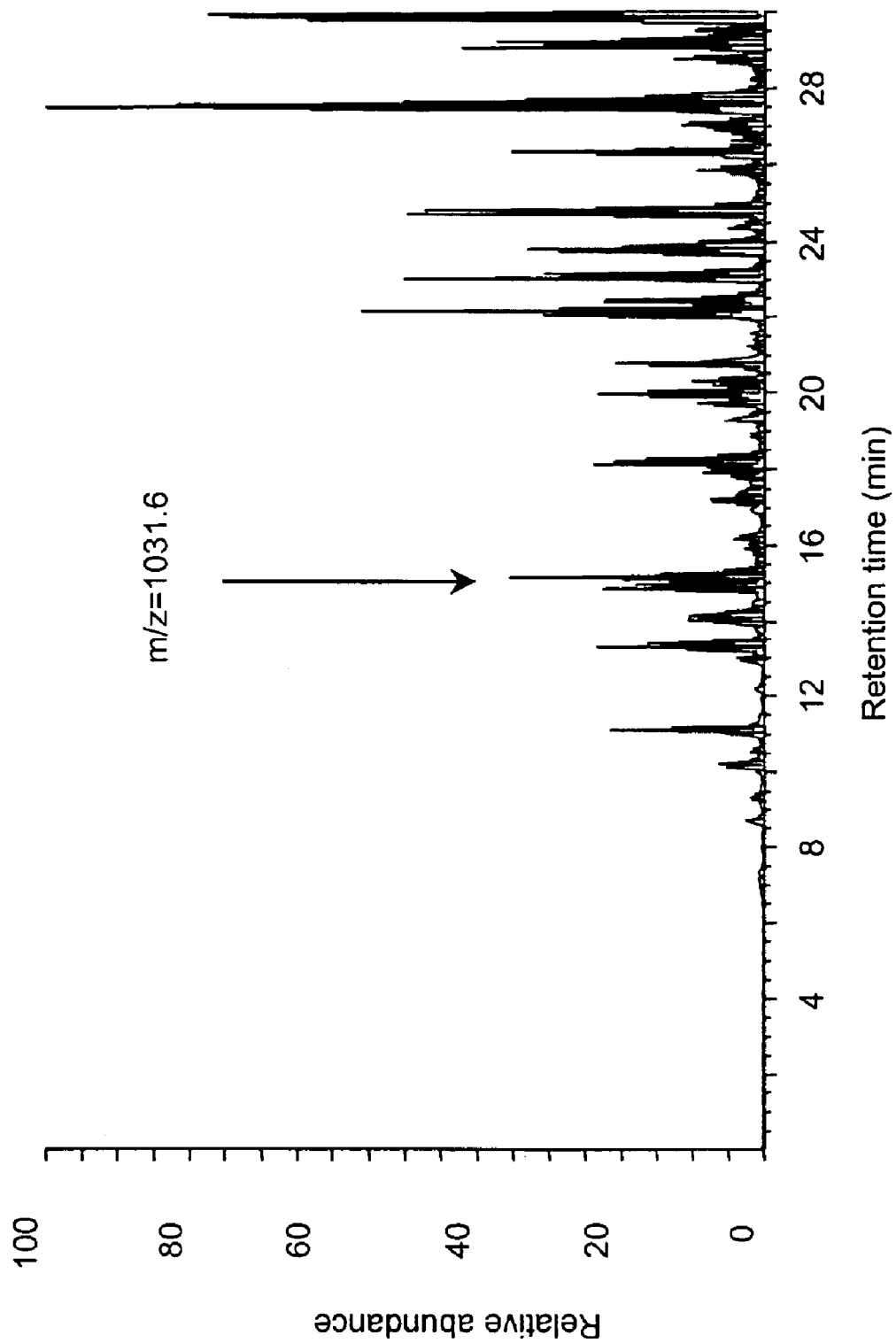
FIGS. 4A–D illustrate the results of application of the phosphopeptide isolation strategy of this invention to the phosphoprotein β-casein. A tryptic digest of β-casein was analyzed by LC-MS/MS both before (FIGS. 4A and 4C) and after (FIGS. 4B and 4D) phosphopeptide isolation according to the procedure of this invention. 10 pmol of starting material was used for phosphopeptide isolation.
Figure 4B:
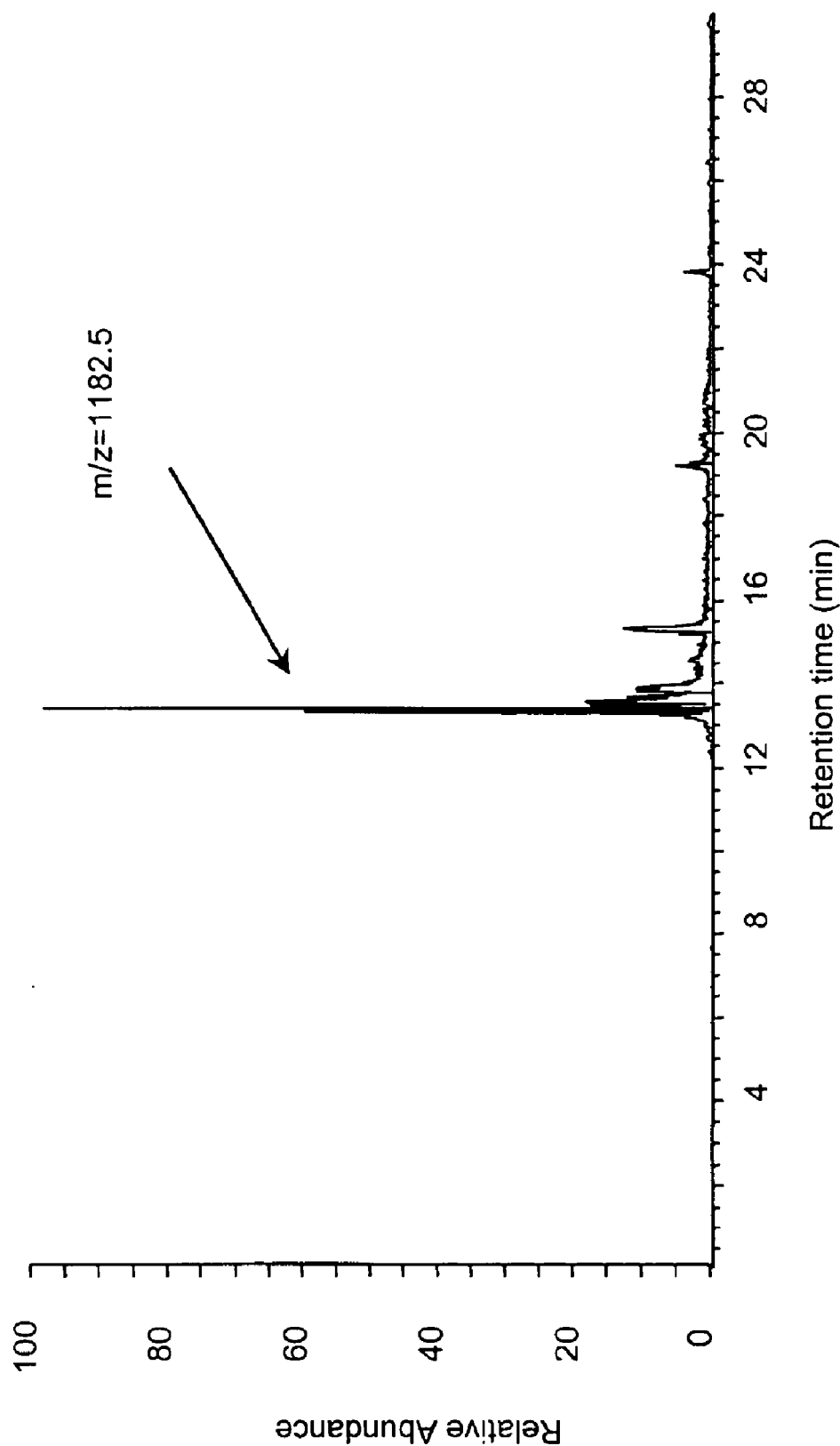
Figure 4C:
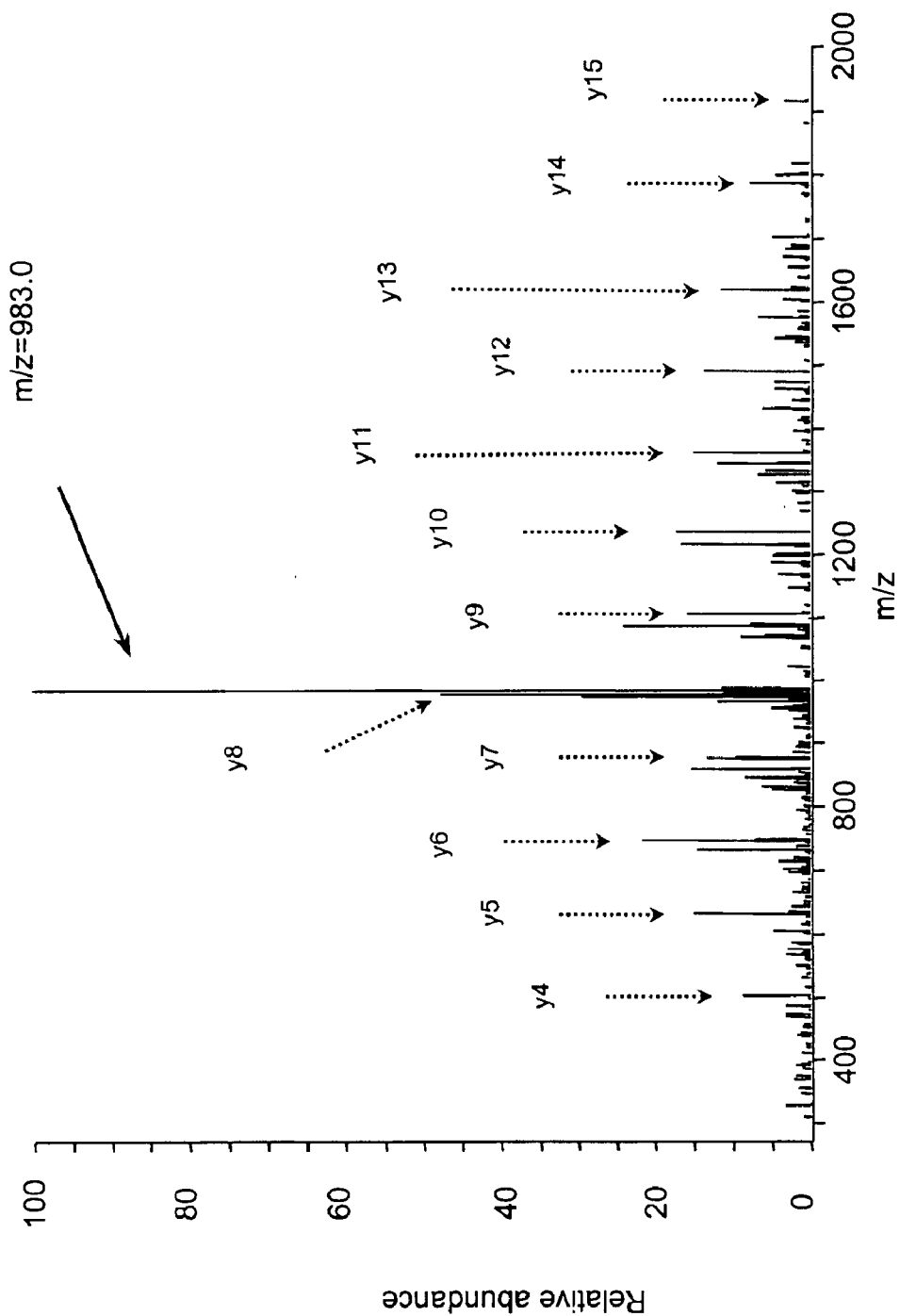

The methods of this invention were also used to purify and detect phosphopeptides from bovine β-casein, a well-characterized phosphoprotein. The peptide was labeled as described in Example 2. A tryptic digest of the phosphoprotein was analyzed by microcapillary LC-MS/MS. As shown in FIG. 4A, numerous peptides were observed for the untreated β-casein digest. The peptide indicated in FIG. 4A was a doubly charged ion at m/z=1031.6. When selected for fragmentation via collision induced dissociation (CID) (FIG. 4C) (Papayannopoulos, I. A. (1995), "The interpretation of collision-induced dissociation tandem mass spectra of peptides," *Mass Spectrometry Rev.* 14,49–73), its fragment ion spectrum exhibited mostly the y-ion series typical for low energy peptide fragmentation and an additional major signal at m/z=983.0 corresponding to a loss of 98 Da due to the loss of the $H_3PO_4$ group from the parent ion(Jonscher, K. R. and Yates, J. R. III (1997), "Matrix-assisted laser desorption ionization/quadrupole ion trap mass spectrometry of peptides. Application to the localization of phosphorylation sites on the P protein from Sendai virus," *J. Biol. Chem.* 272, 1735–1741; Qin, J. & Chait, B. T. (1997), "Identification and characterization of posttranslational modifications of proteins by MALDI ion trap mass spectrometry," *Anal. Chem.* 69, 4002–4009). Database searching of this CID spectrum identified a peptide with sequence FQS*EEQQQTEDELQDK (* denotes a phosphate group). The mass difference between the y13 and y14 ions corresponded to that of phosphoserine, confirming Ser-50 of this protein as the known site of β-casein phosphorylation.

Figure 4D:
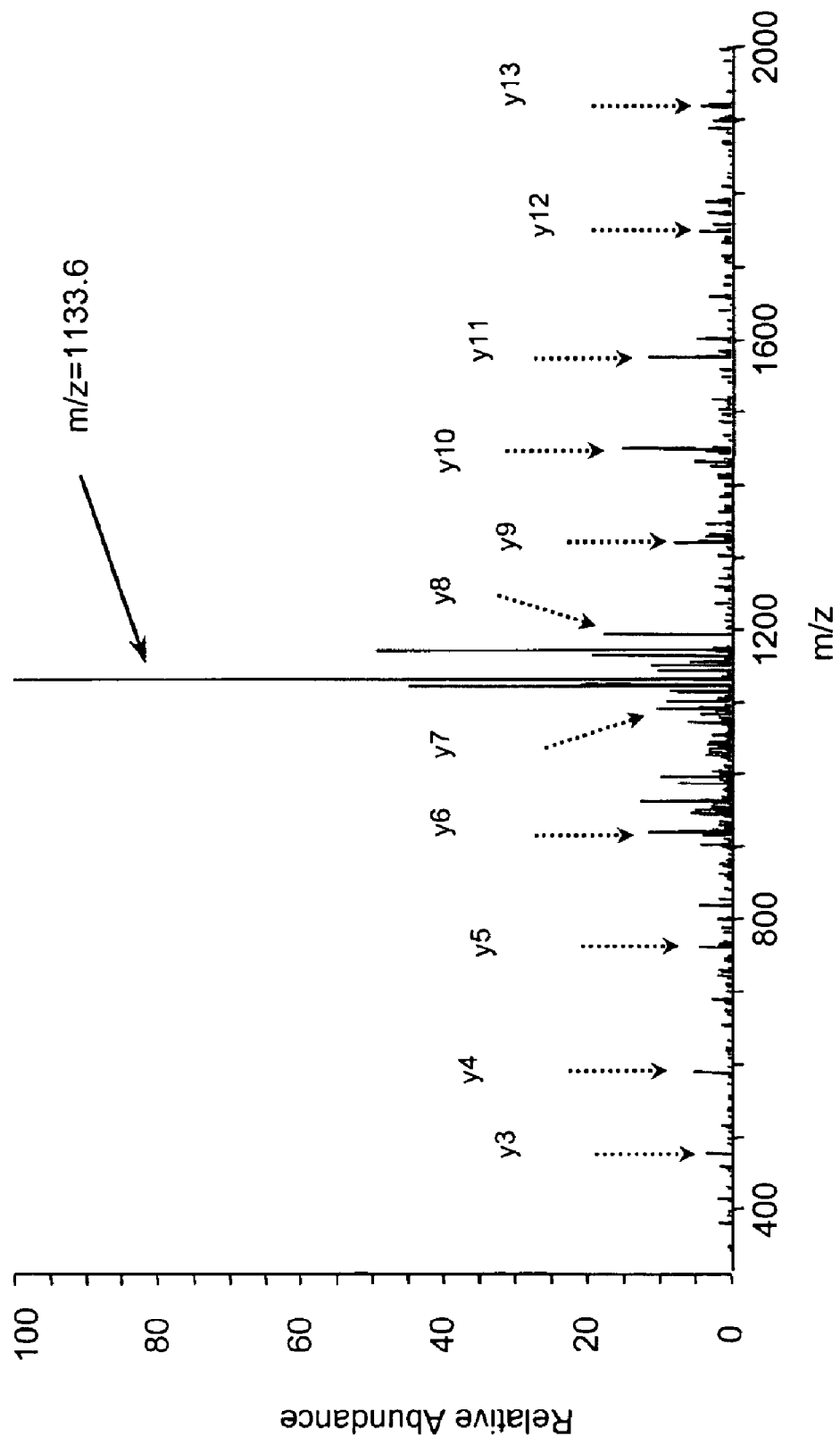

Subjecting the same β-casein digest to the phosphopeptide isolation procedure reduced sample complexity considerably, yielding only one significant doubly charged peptide ion at m/z=1182.5 (FIG. 4D). The CID spectrum of this peptide showed a clear fragment ion series and a major signal at m/z=1133.6 due to the loss of $H_3PO_4$ (FIG. 4D). Database searching of this spectrum identified the same peptide as that in FIG. 4B. The increase in apparent mass for the same peptide (compare FIG. 4A with 4B, and 4C with 4D) is due to quantitative modification on all seven carboxylates (aspartic acid, glutamic acid, and the C terminus) with ethanolamine during the isolation procedure.

Example 4

Sample recovery efficiency for the steps of the invention was examined using a phosphotyrosine-containing peptide, the myelin-basic protein (MBP). MBP was phosphorylated in vitro using the catalytic domain of the tyrosine kinase Lck and radiolabeled ATP (at a known specific activity). The phosphorylated peptide was digested with trypsin and 5 pmol of phosphopeptides were isolated as before, except that the carboxylate groups were blocked with d4-ethanolamine.

Figure 5A:
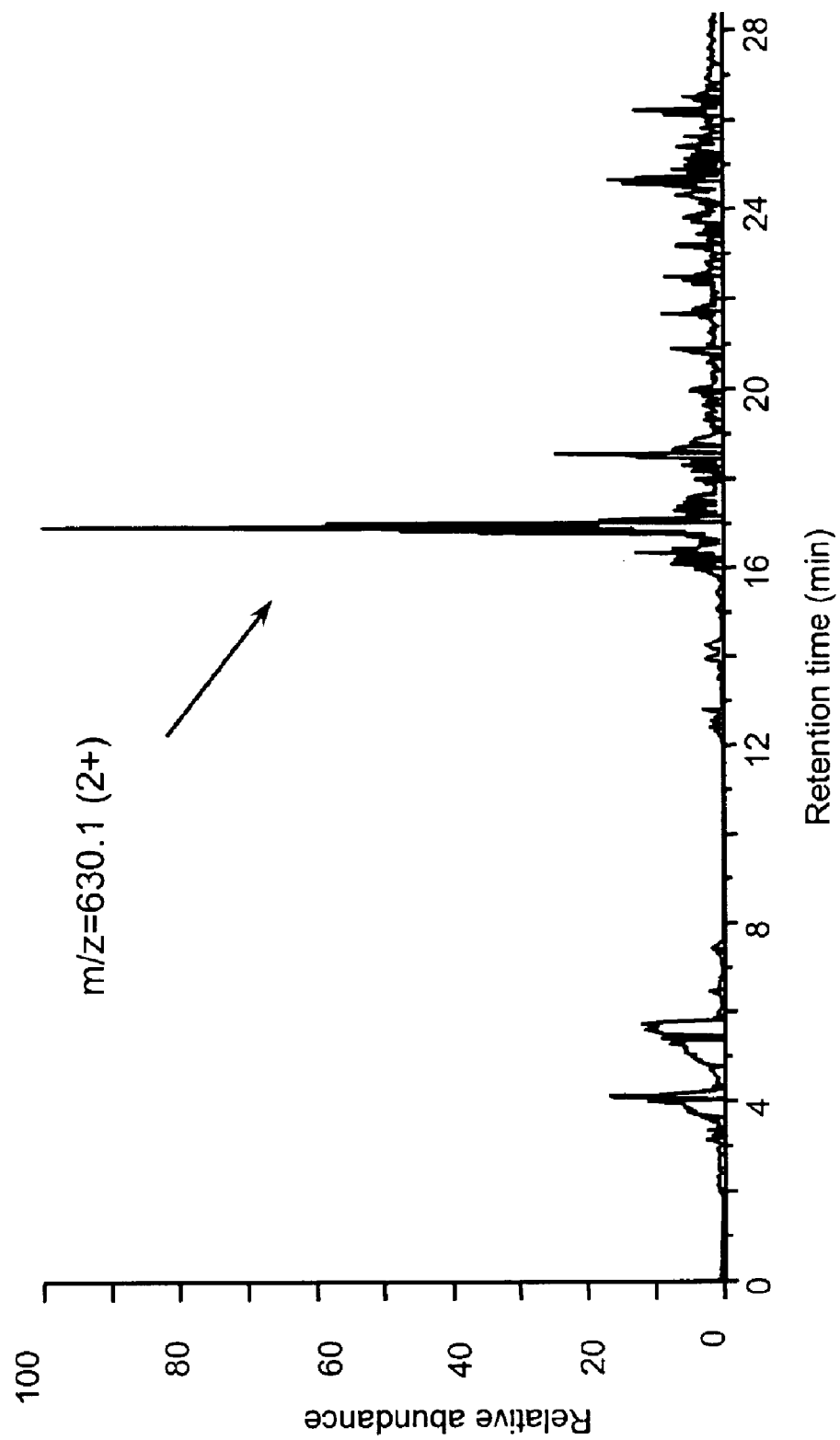
FIGS. 5A and 5B illustrate phosphopeptide isolation from the Lck tyrosine-myelin basic protein (MBP) kinase reaction mixture.
Figure 5B:
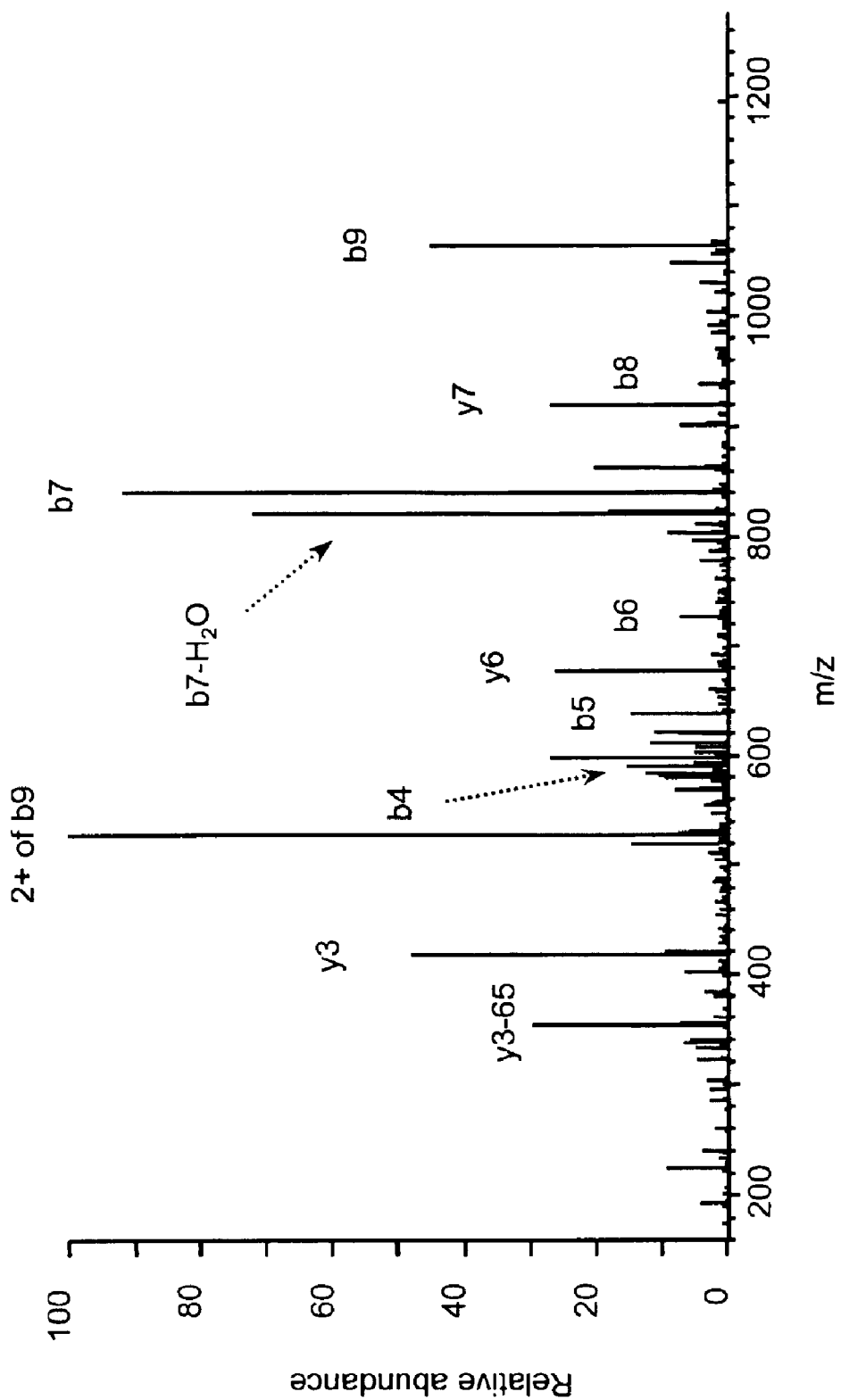

The ion chromatogram for the isolated phosphopeptides is illustrated in FIG. 5A where the most prominent ion at m/2=630.1 (2+) was chosen for fragmentation. The CID of this ion is shown in FIG. 5B. This unambiguously identified phosphopeptide as THY*GSLPQK of MBP(Aebersold, R. et al. (1991), "Determination of the site of tyrosine phosphorylation a the low picomole level by automated solid-phase sequence analysis," Anal. Biochem. 199:51–60). Phospeptide recovery efficiency over the entire six-step procedure was assessed by measuring radioactive counts recovered after each step of the procedure, with a final yield that was consistently about ~20% of the starting material.

In vitro kinase reaction

17 µg of a baculovirally expressed Lck kinase domain-GST (glutathione 5-transferase) fusion protein, 20 µg MBP and 10 µCi of $^{32}$P-containing ATP were incubated at 30° C. for 1 hour in 40 µl of buffer containing 25 mM Tris (pH 7.5), 10 mM $MnCl_2$, 0.25 mM ATP. After 1 hour, 6 M urea was added to stop the reaction. Reduction and alkylation were performed by the addition of dithiothreitol (DTT) at 10 mM for 30 minutes, followed by 2 hours of incubation at 50 mM iodoacetamide. Samples were diluted with water to 1 ml, and 1 µg of trypsin (Promega, Madison, Wis.) was added for 4 hours at 37° C. Peptides were then desalted on a C18 column (Waters, Mass., cat. no. WAT023590) and recovered by elution with 80% acetonitrile/0.1% TFA. Recovered radiolabeled peptides were quantified via Cerenkov counting. From this, an estimated 5 pmol of phosphorylated peptides were taken for isolation of phosphopeptides and evaluation of recovery efficiencies. Deuterated d4-ethanolamine (Isotec, Miamisburg, Ohio) was used to block carboxylate groups in this experiment.

Example 5: Phosphoprotein profiling in yeast

Yeast S. cerevisiae strain (BWGl-7A) was grown till mid-log phase on YPD media with 2% glucose as a carbon source and harvested by centrifugation. Protein extract was prepared by the glass beads method as described in Current Protocols in Molecular Biology (New York, J. Wiley). A mixture of DNAse 1 (20U/ml) and RNAse (10 µg/ml) was added for 30 minutes on ice. Protein concentration was determined using Biorad protein assay and 500 µg of the protein extract was then denatured in 0.1 M potassium phosphate buffer (pH 8.0) with 6 M urea. Proteins were reduced and alkylated by addition of DTT (10 mM, 30 min) followed by 2 hours of incubation with iodoacetamide. Samples were then dialyzed prior to digestion overnight with trypsin at 37°C. The resulting peptide mixture was desalted by reverse phase C18 column as described above. Samples were treated as in Example 1.

Figure 6A:
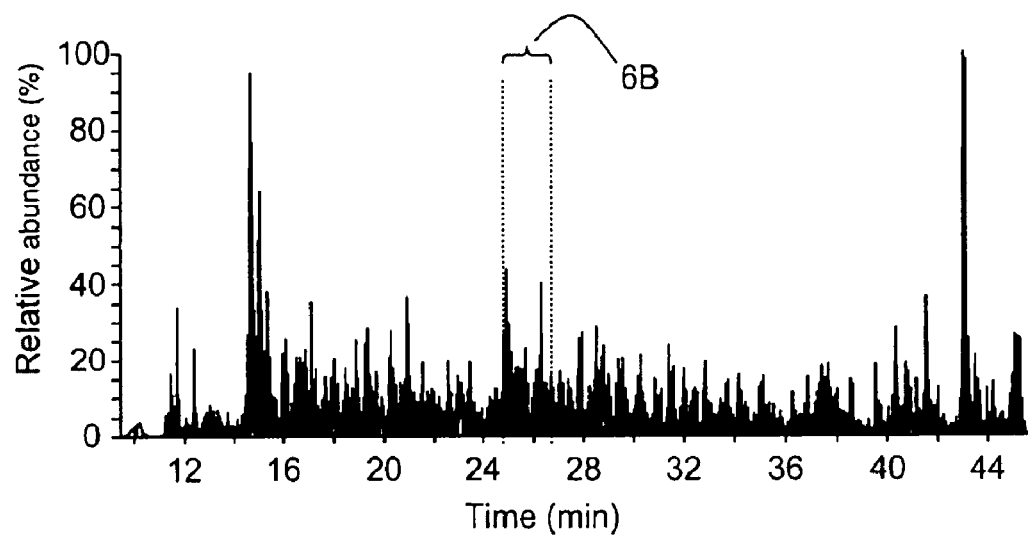
Figure 6B:
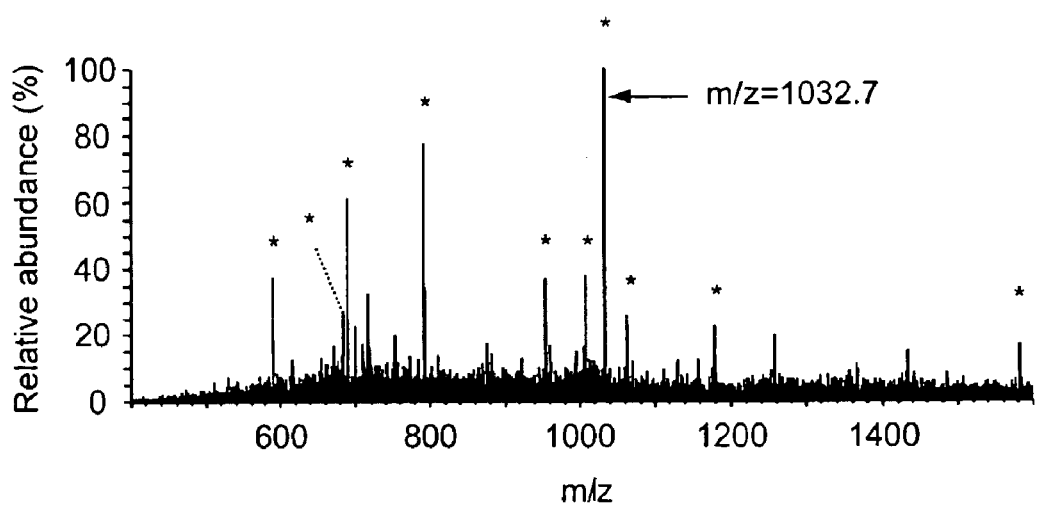

Phosphopeptides were isolated by this method and analyzed by LC-MS/MS, with CID spectra being recorded and searched against the yeast sequence database. FIG. 6A shows the total ion intensity recorded with respect to retention time on the column, indicating the complexity of the sample. FIG. 6B shows the m/z values observed integrated over the time window indicated in FIG. 6A. The major peptide peaks observed which also displayed loss of 98 Da during CID are labeled with an asterisk (*), confirming that the majority of the peptides detected were indeed phosphorylated. Furthermore, the selectivity of the method was apparent by virtue of the fact that over 80% of the CID spectra that led to identification were derived from phosphopeptides. Additionally, CID spectra derived from the few non-phosphorylated peptides identified generally resulted from lower intensity precursors ions. Thus even with a highly complex starting material, only low level of non-specific peptide background carried through the isolation procedure to the MS, affirming its selectivity. In the example shown, the ion at m/z=1032.7 in FIG. 6B was selected for CID, this spectrum being shown in FIG. 6C. In addition to observing a clear fragment ion series, a major signal corresponding to the doubly charged parent ion after undergoing the loss of $H_3PO_4$ is apparent at m/z=983.8.

Following database searching, the peptide was identified as being from enolase and having the sequence indicated in Table 1. This peptide contained three potential threonine phosphorylation sites, and the parent ion mass indicated that the peptide contained a single phosphate group. The y-7 to y-13 ions confirmed that the phosphate was not on the N-terminal threonine. Two possible pairs of the y-5 and y-6 ions correspond to either one of the other two threonine residues being phosphorylated. Thus the exact site of phosphorylation for this peptide could not be determined. Further, the possibility that a mixture of both possible mono-phosphorylated species of this peptide may have co-eluted from the LC column can not be excluded.

Table 1 lists the proteins (and gene names) identified following database searching of the additional CID spectra obtained in the same manner, along with the sequences of the phosphopeptides determined. All peptides positively identified were singly phosphorylated species and they were phosphorylated at serine or threonine residues. Table 1 also indicates the location of the phosphorylation site within the peptide when this could be unequivocally determined, or gives the possible phosphorylation sites in cases in which the observed CID data could not distinguish between two or more phosphorylation sites. As was seen in FIG. 6C, such occasions did not interfere with the identification of the phosphopeptide, and the site of phosphorylation could typically be confined to a cluster of hydroxyl amino acids.

No peptides with multiple serine or threonine phosphorylation sites were identified. In many cases, ions corresponding to loss of $H_3PO_4$ dominated the fragmentation process, resulting in insufficient fragmentation at peptide bonds for sequencing. This effect would be compounded by multiple phosphoserine or phosphothreonine sites in a single peptide. Peptides of too large or small sizes are generally not suitable for MS sequencing; additionally, such peptides could be lost during the desalting steps in this method. Whether this method could completely determine all the phosphorylation sites of a given protein therefore depends on whether phosphorylation sites are contained in peptides of suitable sizes/hydrophobicities for MS analysis, a limitation common to all MS-based methods. In such cases, alternative proteolytic enzymes can be considered. In the experiment on yeast lysate, tyrosine phosphorylated peptides were not identified, likely due to its significantly lower abundance.

Most of the proteins identified were found to be glycolytic enzymes, including enolase, glyceraldehyde 3-phosphate dehydrogenase, phosphoglycerate kinase and pyruvate kinase. Since the cells from which the proteins were isolated utilized glucose as a carbon source, the identification of phosphorylation sites on glycolytic enzymes as being the major species present in this sample is perhaps not surprising. Phosphopeptides from other highly expressed proteins, such as pyruvate decarboxylase isozyme 1, ribosomal proteins and heat shock proteins were also identified. Interestingly, most of the proteins listed in Table 1 were not annotated in the database as being known phosphoproteins. However, previous studies from our group and others identified many of the proteins listed in Table 1 in multiple 2D gel spots (Gygi, S. P. et al. (1999), "Correlation between protein and mRNA abundance in yeast," Mol. Cell. Biol. 19, 1720–1730; Futcher B. et al. (1999) Mol. Cell. Biol. 19, 7357–68), consistent with there being differentially phosphorylated forms of the same protein. These 2D gel data are thus consistent with the identifications made here, supporting the assertion that these proteins are indeed phosphorylated in vivo. Although phosphopeptides from lower abundant, regulatory proteins were not identified in this experiment, the method itself nonetheless is compatible with larger scale sample preparation, or for analysis of enriched protein complexes of interest. Subsequent fractionation either prior to or following this isolation should greatly facilitate identification of lower abundance proteins.

LC-MS/MS and database analysis

An LCQ ion trap mass spectrometer (Finnigan MAT, Calif.) was used with a HP1100 solvent delivery system (Agilent, Calif.). Peptides were pressure-loaded onto the column, then eluted and analyzed by microcapillary LC-MS/MS as described previously (Gygi, S. P. et al. (1999), "Quantitative analysis of complex protein mixtures using isotope-coded affinity tags," Nat. Biotechnol. 17, 994–999). The collision energy for the LCQ was set at 30%. SEQUEST (Eng, J. et al. (1994), "An approach to correlate tandem mass spectral data of peptides with amino acid sequences in a protein database," J. Am. Soc. Mass Spectrom. 5, 976–989) was used for searching yeast YPD database for peptide sequence and identification of site(s) of phosphorylation. Search parameters included differential mass modification to serine, threonine and tyrosine due to phosphorylation, static mass modification to aspartate, glutamate and C-terminus due to the ethanolamine tag, and static mass modification to cysteine due to alkylation by iodoacetamide. Differential mass modification means both possibilities of modified or unmodified amino acid residues were used in database search, while static mass modification means only the modified amino acid residue was used.

Using procedures similar to those outlined above, phosphopeptides were isolated and identified from Jurkat cells. A list of phosphopeptides identified in these experiments is provided in Table 2.

Those of ordinary skill in the art will appreciate that protective groups, labels, reagents, solid phase materials, acid treatments (mild or strong), isotopic labels, purification and washing procedures other than those specifically disclosed herein can be employed to practice the method of this invention. A variety of functional equivalent reagents, methods and techniques in addition to those specifically disclosed herein are known in the art and can be readily employed or adapted without expense of undue experimentation to the practice of this invention. All art-known functional equivalents and known variants of the materials and methods specifically used herein are intended to be encompassed by this invention.

All references cited herein are incorporated by reference herein to the extent that they are not inconsistent herewith.

TABLE 1

Phosphopeptide profile from yeast grown with glucose as a carbon source.

| Gene name[a] | Protein name | Phosphopeptide identified[b] |
| --- | --- | --- |
| ENO1_yeast & ENO2_yeast | Enolase | TAGIQIVADDLT*VT*NPAR[c]<br>IGLDCAS*S*EFFK[c]<br>SGET*EDT*FIADLVVGLR[c] |
| G3P1_yeast | Glyceraldehyde 3-phosphate dehydrogenase | LVSWYDNEYGYS*T*R[c]<br>VIS*NASCTTNCLAPLAK<br>VISNASCT*T*NCLAPLAK[c]<br>TASGNIIPSST*GAAK |
| DCP1_yeast | Pyruvate decarboxylase isozyme 1 | NPVILADACCS*R<br>TPANAAVPAS*T*PLK[c] |
| KPY1_yeast | Pyruvate kinase 1 | GVNLPGTDVDLPALS*EK<br>GVNLPGT*DVDLPALSEK |
| PGK_yeast | Phosphoglycerate kinase | DVT*FLNDCVGPEVEAAVK<br>VLENT*EIGDSIFDK<br>EGIPAGWQGLDNGPES*R<br>ASAPGS*VILLENLR<br>ELPGVAFLS*EK |
| PGM1_yeast | Phosphoglycerate mutase 1 | SFDVPPPPIDASSPFS*QK<br>VYPDVLYT*S*K[c] |
| ALF_yeast | Aldolase | FAIPAINVT*S*S*S*T*AVAALEAAR[c] |
| G6PI_yeast | Glucose-6-phosphate isomerase | EANVT*GLR |
| HS75_yeast | Heat shock protein | SQIDEVVLVGGS*T*R[c] |
| HS72_yeast | Heat shock protein | TTPSFVGFTDT*ER |
| RL11_yeast | 60s ribosomal protein | VLEQLSGQTPVQS*K |
| R141_yeast | 40s ribosomal protein | IEDVTPVPS*DS*T*R[c] |

[a]Gene names are according to Swiss-Prot nomenclature (www.expasy.ch).
[b]Sequence and site of phosphorylation was identified by SEQUEST[18] (see text).
[c]Multiple marks of asterisk indicates ambiguity on the exact site of phosphorylation. All peptides are singly-phosphorylated.
*Indicating site of phosphorylation at the serine or threonine residue to its left.

TABLE 2

Results on phosphoproteins in Jurkat Cells

| | |
|---|---|
| Human GAP SH3 binding protein | SSSPAPADIAQTVQEDLR |
| Tumor necrosis factor type 1 receptor associated protein | GVVDSEDIPLNLSR |
| Thyroid hormone receptor-associated protein complex component TRAP150 mRNA | ASAVSELSPR |
| Stathmin (phosphoprotein p19) | ASGQAFELILSPR |
| Alpha enolase | AAVPSGASTGIYEALELR |
| Glyceraldehyde 3-phosphate dehydrogenase | VPTANVSVVDLTCR |
| Pyruvate kinase | NTGIICTIGPASR |
| L-lactate dehydrogenase h chain | VIGSGCNLDSAR |

We claim:

1. A method for selectively labeling or tagging one or more phosphate groups in a natural or synthetic peptide or protein which also contains one or more carboxylic acid groups or esters thereof which method comprises the steps of:
   a. reacting the natural or synthetic peptide or protein with a protective group that is an amine that reacts to protect the one or more phosphate groups therein by forming phosphoramide bonds and to protect any carboxylic acid groups and esters thereof therein by forming amide bonds;
   b. treating the protected peptide or protein under conditions which selectively substantially cleave the phosphoramide bonds, without substantially cleaving the amide bonds to regenerate one or more free phosphate groups in the peptide or protein; and
   c. reacting the one or more free phosphate groups in the peptide or protein, in which the carboxylic acids groups remain protected, with a label or tag comprising a functional group that reacts with a phosphate group to thereby generate a peptide or protein in which the phosphate groups are selectively labeled or tagged.

2. The method of claim 1 wherein the label or tag is a solid phase material and the one or more free phosphage groups of the peptide or protein are covalently linked to the solid phase material directly or indirectly through a linker moiety.

3. The method of claim 1 wherein the amino group of the protective group that is an amine is reacted with the one or more phosphate groups of the peptide or protein using a carbodiimide catalyzed reaction.

4. The method of claim 2 wherein the one or more free phosphate groups of the peptide or protein are reacted with a linker group wherein the linker group comprises a phosphate reactive group and a second reactive group that functions for forming a covalent bond to the solid phase material.

5. The method of claim 4 wherein the second reactive group is a sulfhydryl reactive group.

6. The method of claim 1 wherein the protective group is ethanolamine.

7. The method of claim 6 wherein in step b the protected peptide or protein is treated with trifluoroacetic acid to selectively regenerate one or more free phosphate groups.

8. The method of claim 1 wherein the one or more free phosphate groups are reacted with a linker which contains a sulfhydryl group or which contains a latent reactive group that can be transformed into a sulfhydryl group.

9. The method of claim 8 wherein the one or more free phosphate groups are first reacted with cystamine and thereafter one or more free sulfhydryl groups are generated by reduction of the disulfide group of the cystamine.

10. The method of claim 9 wherein the disulfide group of the cystamine is reduced using DTT.

11. The method of claim 8 wherein in step c the peptide or protein is covalently attached to a solid support material through reaction with the sulfhydryl group of the linker.

12. The method of claim 11 wherein the solid support material is glass beads with immobilized iodoacetyl groups.

13. The method of claim 1 wherein the natural or synthetic peptide or protein is obtained from a tryptic digest.

14. The method of claim 1 wherein the label or tag is a radiolabel, a fluorescent label, a calorimetric label or an affinity label.

15. The method of claim 1 wherein the label or tag is an affinity label.

16. The method of claim 1 wherein the label or tag is affinity label.

17. The method of claim 1 further comprising a step of detecting the selectively labeled or tagged peptide or protein.

18. The method of claim 17 wherein the selectively labeled or tagged peptide or protein is detected by detection of the label or tag.

19. The method of claim 17 wherein the label or tag is an affinity label and the selectively labeled or tagged peptide or protein is detected by binding to a capture reagent.

20. The method of claim 1 wherein step c comprises attaching the-peptide or protein having one or more free phosphate groups to a solid support or binding the peptide or protein having one or more free phosphate groups to a capture reagent.

21. A method for detecting one or more phosphopeptides or phosphoproteins in one or more samples containing a mixture of peptides, proteins or both, which comprises the steps of:
   a. selectively protecting carboxylic acid groups of the peptides or proteins in the one or more samples by initial reaction with a protecting group that protects both carboxylic acid groups, esters thereof and phosphate groups in the peptides and proteins followed by selective deprotection of the phosphate groups in the peptides and proteins such that any phosphate groups in the peptides or proteins are unprotected
   b. selectively labeling the unprotected phosphate groups in the peptides or proteins in the sample with a label having a functional group that reacts directly or indirectly with a phosphate group; and
   c. detecting the peptides or proteins carrying the selective label of step b to detect the one or more phosphopeptides or phosphoproteins in the sample.

22. The method of claim 21 wherein the carboxylic acid groups, esters thereof and phosphate groups of the peptides or proteins are protected with an amine group that forms amide bonds with carboxylic acid groups and esters thereof and phosphoramide bonds with phosphate groups and wherein the protected phosphate groups are thereafter selectively deprotected by cleavage of the phosphoramide bonds.

23. The method of claim 22 wherein the amide bonds and phosphoramide bonds are formed by carbodiimide-catalyzed condensation reactions.

24. The method of claim 23 wherein the phosphate groups are deprotected without cleavage of the amide bonds by treatment with mild acid.

25. The method of claim 22 wherein the label is a radiolabel, a fluorescent label, a colorimetric label or an affinity label.

26. The method of claim 21 wherein the label is an affinity label and the selectively labeled phosphopeptides or phosphoproteins are detected by binding to a corresponding capture reagent.

27. The method of claim 21 wherein the label is a reactive label.

28. The method of claim 27 wherein the reactive label carries a reactive group that can form a covalent bond to a solid phase material.

29. The method of claim 27 wherein the reactive label carries a latent reactive group.

30. The method of claim 21 further comprising the step of separating selectively labeled phosphopeptides or phosphoproteins from the mixture of peptides or proteins in a sample prior to detection step c.

31. The method of claim 30 wherein the label carries a reactive group that can form a covalent bond to a solid phase material and wherein the selectively labeled phosphopeptides or phosphoproteins are separated by first covalently attaching the labeled phosphopeptides or phosphoproteins to the solid phase material, then washing the solid support to remove peptides or proteins that are not covalently attached to the support and thereafter releasing covalently attached phosphopeptides or phosphoproteins from the solid phase material.

32. The method of claim 31 wherein the phosphopeptides or phosphoproteins released from the solid phase material are detected using mass spectrometric techniques.

33. The method of claim 32 wherein tandem mass spectrometry is used to detect the phosphopeptides or phosphoproteins released from the solid phase.

34. The method of claim 33 wherein tandem mass spectrometry is further used to determine the amino acid sequence of the phosphopeptides or phosphoproteins released from the solid phase and the precise position of the phosphorylated amino acid within the sequence of the phosphopeptides or phosphoproteins.

35. The method of claim 21 for detecting one or more phosphopeptides or phosphoproteins in two or more samples wherein differentially isotopically labeled protecting groups for carboxylic acids or esters thereof are employed with different samples.

36. The method of claim 35 for detecting one or more phosphopeptides or phosphoproteins in two or more samples wherein the labels employed in different samples are differentially isotopically labeled.

37. The method of claim 35 wherein tandem mass spectrometry is used to detect the one or more phosphopeptides or phosphoproteins and the relative amounts of phosphopeptides or phosphoproteins in the two or more samples are determined by measuring the relative amounts of the differentially isotopically labeled labels present.

38. The method of claim 37 wherein combined microcapillary liquid chromatography and tandem mass spectrometry are employed to detect the one or more phosphopeptides or phosphoproteins.

39. The method of claim 1 wherein the amine is a hydroxy amine.

40. The method of claim 1 wherein the protective group is a differentially isotopically labeled protecting group.

41. The method of claim 40 wherein the protective group is a hydroxy amine.

42. The method of claim 40 wherein the protective group is differentially isotopically labeled using deuterium.

43. The method of claim 21 for detecting one or more phosphopeptides in two or more samples wherein differentially isotopically labeled ethanolamine is used to protect the carboxylic acid groups of peptides in different samples.

44. The method of claim 21 further comprising a step of determining the sequence of one or more phosphopeptides detected.

45. The method of claim 44 wherein the sequence of the phosphopeptide is determined by tandem mass spectrometry.

46. The method of claim 45 wherein the samples are protein digests containing peptides and the sequence of the phosphopeptide detected is used to identify the protein from which the phosphopeptide is derived.

47. The method of claim 21 in which the amount of one or more phosphoproteins in a sample is also determined by mass spectrometry, and which further comprises the step of introducing into a sample a known amount of one or more internal standards for each of the phosphoproteins to be quantitated.

48. The method of claim 47 in which different samples represent proteins expressed in response to different environmental or nutritional conditions, different chemical or physical stimuli or at different times.

49. The method of claim 21 wherein phosphopeptides or phosphoproteins in different samples are labeled with different fluorescent labels and the relative amounts of a labeled phosphopeptide or phosphoprotein in different samples can be measured by measuring the relative intensity of the fluorescence emission of a labeled phosphopeptide or phosphoprotein in different samples.

50. The method of claim 1 further comprising a step of protecting any amine groups in the peptide or protein prior to step a.

51. The method of claim 50 wherein the amine groups are protected with t-boc or f-moc.

52. The method of claim 21 further comprising a step of protecting any amine groups in peptides or proteins of the one or more samples prior to step a.

53. The method of claim 52 wherein the amine groups of peptides or proteins of the one or more samples are protected with t-boc or f-moc.

54. The method of claim 20 wherein the peptide or protein having one or more free phosphate groups is present in a mixture containing peptides or proteins that do not contain phosphate groups and which further comprising a step of separating peptides or proteins in which the phosphate groups are selectively labeled or tagged from peptides or proteins that do not contain phosphate groups.

55. The method of claim 54 wherein the peptide or protein in which the phosphate groups are selectively labeled or tagged is attached to a solid support and the peptide or protein attached to the solid support is separated from peptides and proteins not attached to the support.

56. The method of claim 54 wherein the peptide or protein in which the phosphate groups are selectively labeled or tagged comprises an affinity label which is attached to a capture reagent and the peptide or protein attached to the capture reagent is separated from peptides and proteins not attached to the capture reagent.

57. The method of claim 21 for detection of one or more phosphopeptides.

58. The method of claim 21 wherein the mixture of peptides and proteins of the one or more samples is obtained from a tryptic digest.

59. The method of claim 26 wherein the label is a reactive label.

60. A method for detecting one or more phosphopeptides or phosphoproteins in one or more samples containing a mixture of peptides or proteins which comprises the steps of:
   a. reacting the peptides or proteins in the mixture with a protective group that is an amine that reacts to protect any phosphate groups therein by forming phosphoramide bonds and to protect any carboxylic acid groups and esters thereof therein by forming amide bonds;
   b. treating the protected peptides or proteins in the mixture under conditions which selectively substantially cleave the phosphoramide bonds, without substantially cleaving the amide bonds, to regenerate free phosphate groups in the peptide or protein;
   c. selectively labeling the free phosphate groups in the peptides or proteins in the sample with a label having a functional group that reacts directly or indirectly with a phosphate group; and
   d. detecting the peptides or proteins carrying the selective label of step c to detect the one or more phosphopeptides or phosphoproteins in the sample.

61. The method of claim 60 wherein the protective group is ethanol amine.

* * * * *

SEQUENCE LISTING

```
<160> NUMBER OF SEQ ID NOS: 34

<210> SEQ ID NO 1
<211> LENGTH: 9
<212> TYPE: PRT
<213> ORGANISM: bovine

<400> SEQUENCE: 1

Thr His Tyr Gly Ser Leu Pro Gln Lys
 1               5

<210> SEQ ID NO 2
<211> LENGTH: 18
<212> TYPE: PRT
<213> ORGANISM: Saccharomyces cerevisiae

<400> SEQUENCE: 2

Thr Ala Gly Ile Gln Ile Val Ala Asp Asp Leu Thr Val Thr Asn Pro
 1               5                  10                  15

Ala Arg

<210> SEQ ID NO 3
<211> LENGTH: 16
<212> TYPE: PRT
<213> ORGANISM: bovine

<400> SEQUENCE: 3

Phe Gln Ser Glu Glu Gln Gln Thr Glu Asp Glu Leu Gln Asp Lys
 1               5                  10                  15

<210> SEQ ID NO 4
<211> LENGTH: 12
<212> TYPE: PRT
<213> ORGANISM: Saccharomyces cerevisiae

<400> SEQUENCE: 4

Ile Gly Leu Asp Cys Ala Ser Ser Glu Phe Phe Lys
 1               5                  10

<210> SEQ ID NO 5
<211> LENGTH: 17
<212> TYPE: PRT
<213> ORGANISM: Saccharomyces cerevisiae

<400> SEQUENCE: 5
```

-continued

Ser Gly Glu Thr Glu Asp Thr Phe Ile Ala Asp Leu Val Val Gly Leu
 1               5                   10                  15
Arg

<210> SEQ ID NO 6
<211> LENGTH: 14
<212> TYPE: PRT
<213> ORGANISM: Saccharomyces cerevisiae

<400> SEQUENCE: 6

Leu Val Ser Trp Tyr Asp Asn Glu Tyr Gly Tyr Ser Thr Arg
 1               5                   10

<210> SEQ ID NO 7
<211> LENGTH: 17
<212> TYPE: PRT
<213> ORGANISM: Saccharomyces cerevisiae

<400> SEQUENCE: 7

Val Ile Ser Asn Ala Ser Cys Thr Thr Asn Cys Leu Ala Pro Leu Ala
 1               5                   10                  15
Lys

<210> SEQ ID NO 8
<211> LENGTH: 17
<212> TYPE: PRT
<213> ORGANISM: Saccharomyces cerevisiae

<400> SEQUENCE: 8

Val Ile Ser Asn Ala Ser Cys Thr Thr Asn Cys Leu Ala Pro Leu Ala
 1               5                   10                  15
Lys

<210> SEQ ID NO 9
<211> LENGTH: 15
<212> TYPE: PRT
<213> ORGANISM: Saccharomyces cerevisiae

<400> SEQUENCE: 9

Thr Ala Ser Gly Asn Ile Ile Pro Ser Ser Thr Gly Ala Ala Lys
 1               5                   10                  15

<210> SEQ ID NO 10
<211> LENGTH: 12
<212> TYPE: PRT
<213> ORGANISM: Saccharomyces cerevisiae

<400> SEQUENCE: 10

Asn Pro Val Ile Leu Ala Asp Ala Cys Cys Ser Arg
 1               5                   10

<210> SEQ ID NO 11
<211> LENGTH: 14
<212> TYPE: PRT
<213> ORGANISM: Saccharomyces cerevisiae

<400> SEQUENCE: 11

Thr Pro Ala Asn Ala Ala Val Pro Ala Ser Thr Pro Leu Lys
 1               5                   10

<210> SEQ ID NO 12
<211> LENGTH: 17
<212> TYPE: PRT

<213> ORGANISM: Saccharomyces cerevisiae

<400> SEQUENCE: 12

Gly Val Asn Leu Pro Gly Thr Asp Val Asp Leu Pro Ala Leu Ser Glu
1               5                   10                  15
Lys

<210> SEQ ID NO 13
<211> LENGTH: 17
<212> TYPE: PRT
<213> ORGANISM: Saccharomyces cerevisiae

<400> SEQUENCE: 13

Gly Val Asn Leu Pro Gly Thr Asp Val Asp Leu Pro Ala Leu Ser Glu
1               5                   10                  15
Lys

<210> SEQ ID NO 14
<211> LENGTH: 18
<212> TYPE: PRT
<213> ORGANISM: Saccharomyces cerevisiae

<400> SEQUENCE: 14

Asp Val Thr Phe Leu Asn Asp Cys Val Gly Pro Glu Val Glu Ala Ala
1               5                   10                  15
Val Lys

<210> SEQ ID NO 15
<211> LENGTH: 14
<212> TYPE: PRT
<213> ORGANISM: Saccharomyces cerevisiae

<400> SEQUENCE: 15

Val Leu Glu Asn Thr Glu Ile Gly Asp Ser Ile Phe Asp Lys
1               5                   10

<210> SEQ ID NO 16
<211> LENGTH: 17
<212> TYPE: PRT
<213> ORGANISM: Saccharomyces cerevisiae

<400> SEQUENCE: 16

Glu Gly Ile Pro Ala Gly Trp Gln Gly Leu Asp Asn Gly Pro Glu Ser
1               5                   10                  15
Arg

<210> SEQ ID NO 17
<211> LENGTH: 14
<212> TYPE: PRT
<213> ORGANISM: Saccharomyces cerevisiae

<400> SEQUENCE: 17

Ala Ser Ala Pro Gly Ser Val Ile Leu Leu Glu Asn Leu Arg
1               5                   10

<210> SEQ ID NO 18
<211> LENGTH: 11
<212> TYPE: PRT
<213> ORGANISM: Saccharomyces cerevisiae

<400> SEQUENCE: 18

Glu Leu Pro Gly Val Ala Phe Leu Ser Glu Lys

```
<210> SEQ ID NO 19
<211> LENGTH: 18
<212> TYPE: PRT
<213> ORGANISM: Saccharomyces cerevisiae

<400> SEQUENCE: 19

Ser Phe Asp Val Pro Pro Pro Ile Asp Ala Ser Ser Pro Phe Ser
 1               5                  10                  15
Gln Lys

<210> SEQ ID NO 20
<211> LENGTH: 10
<212> TYPE: PRT
<213> ORGANISM: Saccharomyces cerevisiae

<400> SEQUENCE: 20

Val Tyr Pro Asp Val Leu Tyr Thr Ser Lys
 1               5                  10

<210> SEQ ID NO 21
<211> LENGTH: 22
<212> TYPE: PRT
<213> ORGANISM: Saccharomyces cerevisiae

<400> SEQUENCE: 21

Phe Ala Ile Pro Ala Ile Asn Val Thr Ser Ser Ser Thr Ala Val Ala
 1               5                  10                  15
Ala Leu Glu Ala Ala Arg
            20

<210> SEQ ID NO 22
<211> LENGTH: 8
<212> TYPE: PRT
<213> ORGANISM: Saccharomyces cerevisiae

<400> SEQUENCE: 22

Glu Ala Asn Val Thr Gly Leu Arg
 1               5

<210> SEQ ID NO 23
<211> LENGTH: 14
<212> TYPE: PRT
<213> ORGANISM: Saccharomyces cerevisiae

<400> SEQUENCE: 23

Ser Gln Ile Asp Glu Val Val Leu Val Gly Gly Ser Thr Arg
 1               5                  10

<210> SEQ ID NO 24
<211> LENGTH: 13
<212> TYPE: PRT
<213> ORGANISM: Saccharomyces cerevisiae

<400> SEQUENCE: 24

Thr Thr Pro Ser Phe Val Gly Phe Thr Asp Thr Glu Arg
 1               5                  10

<210> SEQ ID NO 25
<211> LENGTH: 14
<212> TYPE: PRT
<213> ORGANISM: Saccharomyces cerevisiae
```

-continued

```
<400> SEQUENCE: 25

Val Leu Glu Gln Leu Ser Gly Gln Thr Pro Val Gln Ser Lys
 1               5                  10

<210> SEQ ID NO 26
<211> LENGTH: 13
<212> TYPE: PRT
<213> ORGANISM: Saccharomyces cerevisiae

<400> SEQUENCE: 26

Ile Glu Asp Val Thr Pro Val Pro Ser Asp Ser Thr Arg
 1               5                  10

<210> SEQ ID NO 27
<211> LENGTH: 18
<212> TYPE: PRT
<213> ORGANISM: Homo sapiens

<400> SEQUENCE: 27

Ser Ser Ser Pro Ala Pro Ala Asp Ile Ala Gln Thr Val Gln Glu Asp
 1               5                  10                  15

Leu Arg

<210> SEQ ID NO 28
<211> LENGTH: 14
<212> TYPE: PRT
<213> ORGANISM: Homo sapiens

<400> SEQUENCE: 28

Gly Val Val Asp Ser Glu Asp Ile Pro Leu Asn Leu Ser Arg
 1               5                  10

<210> SEQ ID NO 29
<211> LENGTH: 10
<212> TYPE: PRT
<213> ORGANISM: Homo sapiens

<400> SEQUENCE: 29

Ala Ser Ala Val Ser Glu Leu Ser Pro Arg
 1               5                  10

<210> SEQ ID NO 30
<211> LENGTH: 13
<212> TYPE: PRT
<213> ORGANISM: Homo sapiens

<400> SEQUENCE: 30

Ala Ser Gly Gln Ala Phe Glu Leu Ile Leu Ser Pro Arg
 1               5                  10

<210> SEQ ID NO 31
<211> LENGTH: 18
<212> TYPE: PRT
<213> ORGANISM: Homo sapiens

<400> SEQUENCE: 31

Ala Ala Val Pro Ser Gly Ala Ser Thr Gly Ile Tyr Glu Ala Leu Glu
 1               5                  10                  15

Leu Arg

<210> SEQ ID NO 32
<211> LENGTH: 14
<212> TYPE: PRT
```

-continued

```
<213> ORGANISM: Homo sapiens

<400> SEQUENCE: 32

Val Pro Thr Ala Asn Val Ser Val Val Asp Leu Thr Cys Arg
 1               5                  10

<210> SEQ ID NO 33
<211> LENGTH: 13
<212> TYPE: PRT
<213> ORGANISM: Homo sapiens

<400> SEQUENCE: 33

Asn Thr Gly Ile Ile Cys Thr Ile Gly Pro Ala Ser Arg
 1               5                  10

<210> SEQ ID NO 34
<211> LENGTH: 12
<212> TYPE: PRT
<213> ORGANISM: Homo sapiens

<400> SEQUENCE: 34

Val Ile Gly Ser Gly Cys Asn Leu Asp Ser Ala Arg
 1               5                  10
```